United States Patent
Li et al.

(10) Patent No.: US 9,073,936 B2
(45) Date of Patent: Jul. 7, 2015

(54) ORGANIC COMPOUNDS

(71) Applicants: Peng Li, New York, NY (US); Hailin Zheng, New York, NY (US); Jun Zhao, New York, NY (US); Lawrence P. Wennogle, New York, NY (US)

(72) Inventors: Peng Li, New York, NY (US); Hailin Zheng, New York, NY (US); Jun Zhao, New York, NY (US); Lawrence P. Wennogle, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 14/209,258

(22) Filed: Mar. 13, 2014

(65) Prior Publication Data

US 2014/0275131 A1    Sep. 18, 2014

Related U.S. Application Data

(60) Provisional application No. 61/788,551, filed on Mar. 15, 2013.

(51) Int. Cl.
    C07D 487/14    (2006.01)

(52) U.S. Cl.
    CPC .................................... C07D 487/14 (2013.01)

(58) Field of Classification Search
    CPC ...................................................... C07D 487/14
    USPC ............................................ 514/267; 544/251
    See application file for complete search history.

(56) References Cited

U.S. PATENT DOCUMENTS

| | | | |
|---|---|---|---|
| 5,202,328 A | 4/1993 | de Laszlo et al. |
| 5,294,612 A | 3/1994 | Bacon et al. |
| 5,393,755 A | 2/1995 | Neustadt et al. |
| 5,824,683 A | 10/1998 | McKittrick et al. |
| 5,849,770 A | 12/1998 | Head et al. |
| 5,939,419 A | 8/1999 | Tulshian et al. |
| 5,962,492 A | 10/1999 | Warrellow et al. |
| 6,013,621 A | 1/2000 | Nishi et al. |
| 6,133,273 A | 10/2000 | Gilbert et al. |
| 6,235,742 B1 | 5/2001 | Bell et al. |
| 6,235,746 B1 | 5/2001 | Davis et al. |
| 6,316,444 B1 | 11/2001 | Hunt et al. |
| 6,423,716 B1 | 7/2002 | Matsuno et al. |
| 6,492,371 B2 | 12/2002 | Roylance |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,649,608 B2 | 11/2003 | Pease et al. |
| 6,670,368 B1 | 12/2003 | Breault et al. |
| 6,693,099 B2 | 2/2004 | Degenhardt et al. |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,157,451 B2 | 1/2007 | Atwal et al. |
| 8,273,750 B2 | 9/2012 | Li et al. |
| 8,273,751 B2 | 9/2012 | Li et al. |
| 8,536,159 B2 | 9/2013 | Li et al. |
| 8,633,180 B2 | 1/2014 | Li et al. |
| 8,664,207 B2 | 3/2014 | Li et al. |
| 8,697,710 B2 | 4/2014 | Li et al. |
| 2003/0069246 A1 | 4/2003 | Darrow et al. |
| 2003/0092908 A1 | 5/2003 | Pitts et al. |
| 2003/0162782 A1 | 8/2003 | Grossman et al. |
| 2004/0087517 A1 | 5/2004 | Burnet et al. |
| 2004/0259792 A1 | 12/2004 | Palmer et al. |
| 2005/0075795 A1 | 4/2005 | Pandit |
| 2005/0113379 A1 | 5/2005 | Ge et al. |
| 2006/0252790 A1 | 11/2006 | Allen et al. |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2010/0087450 A1 | 4/2010 | Mates et al. |
| 2010/0173878 A1 | 7/2010 | Li et al. |
| 2010/0273753 A1 | 10/2010 | Li et al. |
| 2010/0273754 A1 | 10/2010 | Li |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li |
| 2012/0238589 A1 | 9/2012 | Li et al. |
| 2013/0018063 A1* | 1/2013 | Li et al. ................... 514/267 |
| 2013/0085123 A1 | 4/2013 | Li et al. |
| 2013/0239234 A1 | 9/2013 | Greengard et al. |
| 2013/0324565 A1 | 12/2013 | Li et al. |

(Continued)

FOREIGN PATENT DOCUMENTS

DE    19931206 A1    1/2001
EP    0 063 381 A1    10/1982

(Continued)

OTHER PUBLICATIONS

U.S. Appl. No. 14/125,017, filed Mar. 17, 2014, Li et al.
U.S. Appl. No. 14/252,511, filed Apr. 14, 2014, Li et al.
Ahn, H. et al., "Potent Tetracyclic Guanine Inhibitors of PDE1 and PDE5 Cyclic Guanosine Monophosphate Phosphodiesterases with Oral Antihypertensive Activity," Journal of Medicinal Chemistry, 1997, 40 (14), 2196-2210.
Al-Afaleq, E. et al., "Heterocyclic o-Aminonitriles: Preparation of Pyrazolo[3,4-d]-pyrimidines with Modification of the Substituents at the 1-Position," Molecules, 2001, 6, 621-638.
"Anxiety," [retrieved on May 14, 2008]. Retrieved online via Internet, URL: http://www.nlm.nih.gov/medlineplus/anxiety.html, 5 pages.

(Continued)

Primary Examiner — Erich A Leeser
(74) Attorney, Agent, or Firm — Hoxie & Associates LLC

(57) ABSTRACT

Provided are PDE1 inhibitors of Formula I, processes for their production, their use as pharmaceuticals, and pharmaceutical compositions comprising them.

22 Claims, No Drawings

(56) References Cited

U.S. PATENT DOCUMENTS

| | | |
|---|---|---|
| 2013/0331363 A1 | 12/2013 | Li et al. |
| 2013/0338124 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |

FOREIGN PATENT DOCUMENTS

| | | | |
|---|---|---|---|
| EP | 0 095 289 A2 | 11/1983 | |
| EP | 0 201 188 A2 | 12/1986 | |
| EP | 0 636 626 A1 | 2/1995 | |
| EP | 0 911 333 A1 | 4/1999 | |
| JP | 53031694 A | 3/1978 | |
| KR | 10-1991-0006866 | 9/1991 | |
| WO | WO 91/19717 A1 | 12/1991 | |
| WO | WO 94/19351 A1 | 9/1994 | |
| WO | WO 98/46606 A1 | 10/1998 | |
| WO | WO 98/52568 A1 | 11/1998 | |
| WO | WO 01/27113 A2 | 4/2001 | |
| WO | WO 02/074312 A1 | 9/2002 | |
| WO | WO 03/002567 A1 | 1/2003 | |
| WO | WO 03/020702 A2 | 3/2003 | |
| WO | WO 03/020724 A1 | 3/2003 | |
| WO | WO 03/042216 A1 | 5/2003 | |
| WO | WO 2006/133261 A2 | 12/2006 | |
| WO | WO 2006133261 | * 12/2006 | ........... C07D 239/00 |
| WO | WO 2007/143568 A1 | 12/2007 | |
| WO | WO 2007/143705 A2 | 12/2007 | |
| WO | WO 2008/063505 A1 | 5/2008 | |
| WO | WO 2009/073210 A1 | 6/2009 | |
| WO | WO 2009/075784 A1 | 6/2009 | |
| WO | WO 2011/043816 A1 | 4/2011 | |
| WO | WO 2011/153129 A1 | 12/2011 | |
| WO | WO 2011/153135 A1 | 12/2011 | |
| WO | WO 2011/153136 A1 | 12/2011 | |
| WO | WO 2011/153138 A1 | 12/2011 | |
| WO | WO 2012/171016 A1 | 12/2012 | |
| WO | WO 2013/192556 A2 | 12/2013 | |

OTHER PUBLICATIONS

Aswar, M. et al., "Anti-Cataleptic Activity of Various Extracts of *Ocimum Sanctum*," International Journal of Pharmaceutical Research and Development, 2010, 2 (6), 7 pages.

"Autism," [retrieved on May 14, 2008]. Retrieved online via Internet, URL: http://www.nlm.nih.gov/medlineplus/autism.html, 6 pages.

Banker, Gilbert S. et al., Eds., Modern Pharmaceutics, Third Edition, Marcel Dekker Inc., New York, 1996.

Bastia, E. et al., "Effect of $A_1$ and $A_{2A}$ Adenosine Receptor Ligands in Mouse Acute Models of Pain," Neuroscience Letters, 2002, 328, 241-244.

Bender, A. et al., "Cyclic Nucleotide Phosphodiesterases: Molecular Regulation to Clinical Use," Pharmacological Reviews, 2006, 58 (3), 488-520.

Blokland, A. et al., "PDE Inhibition and Cognition Enhancement," 2012, 22 (4), 349-354 (abstract only).

Boyd, K. et al., "Dopamine Receptor Signaling and Current and Future Antipsychotic Drugs" in Current Antipsychotics, Handbook of Experimental Pharmacology, 212, Gross, G. et al., Eds., doi:10.1007/978-3-642-25761-2_3, Springer-Verlag, Berlin, 2012, pp. 53-86.

Burnouf, C. et al., "Synthesis, Structure-Activity Relationships, and Pharmacological Profile of 9-Amino-4-oxo-1-phenyl-3,4,6,7-tetrahydro[1,4]diazepino[6,7,1-*hi*]indoles: Discovery of Potent, Selective Phosphodiesterase Type 4 Inhibitors," Journal of Medicinal Chemistry, 2000, 43 (25), 4850-4867.

Chalimoniuk, M. et al., "Upregulation of Guanylyl Cyclase Expression and Activity in Striatum of MPTP-induced Parkinsonism in Mice," Biochemical and Biophysical Research Communications, 2004, 324, 118-126.

Chebib, M. et al., "1-Phenylpyrazolo[3,4-*d*]pyrimidines; Structure-Activity Relationships for C6 Substituents at $A_1$ and $A_{2A}$ Adenosine Receptors," Bioorganic & Medicinal Chemistry, 2000, 8, 2581-2590.

Chen, M. et al., "Effects of Bimatoprost 0.03% on Ocular Hemodynamics in Normal Tension Glaucoma," Journal of Ocular Pharmacology and Therapeutics, 2006, 22 (3), 188-193.

Chermat, R. et al., "Adaptation of the Tail Suspension Test to the Rat," Journal de Pharmacologic (Paris), 1986, 17 (3), 348-350.

Deshmukh, R. et al., "Amelioration of Intracerebroventricular Streptozotocin Induced Cognitive Dysfunction and Oxidative Stress by Vinpocetine—A PDE1 Inhibitor," European Journal of Pharmacology, 2009, 620 (1-3), 49-56.

Dewald, H. et al., "Synthesis and Potential Antipsychotic Activity of 1*H*-Imidazo[1,2-*c*]pyrazolo[3,4-*e*]pyrimidines," Journal of Medicinal Chemistry, 1988, 31, 454-461.

Ehrman, L. et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice," Genes, Brain and Behavior, 2006, 5 (7), 540-551.

Ennaceur, A. et al., "A New One-Trial Test for Neurobiological Studies of Memory in Rats. 1:Behavioral Data," Behavioural Brain Research, 1998, 31, 47-59.

Fienberg, A. et al., "DARPP-32: Regulator of the Efficacy of Dopaminergic Neurotransmission," Science, 1998, 281, 838-842.

Filgueiras, C. et al., "Phosphodiesterase Type 1 Inhibition Improves Learning in Rats Exposed to Alcohol During the Third Trimester Equivalent of Human Gestation," Neuroscience Letters, 2010, 473 (3), 202-207.

Gelbin, M. et al., "Ketene-S,N-acetals as Synthons for Heterocycles, New Synthesis of Pyrimidinones," Journal Für Praktische Chemie, 1987, 329 (5), 753-766.

Goodman & Gilman, Las bases farmacológicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.

Greengard, P. et al., "Beyond the Dopamine Receptor: the DARPP-32/Protein Phosphatase-1 Cascade," Neuron, 1999, 23, 435-447.

Han, P. et al., "The Calcium/Calmodulin-dependent Phosphodiesterase PDE1C Down-regulates Glucose-induced Insulin Secretion," The Journal of Biological Chemistry, 1999, 274 (32), 22337-22344.

Hulley, P. et al., "Cyclic AMP Promotes the Survival of Dopaminergic Neurons in vitro and Protects Them from the Toxic Effects of $MPP^+$," Journal of Neural Transmission [Supplementa], 1995, 46, 217-228.

Japanese Patent Office, Patent Abstracts of Japan, Abstract for JP 53031694 A, Date of publication of application Mar. 25, 1978, 1 page.

Jiang, M. et al., "Chemoenzymatic Asymmetric Total Synthesis of Phosphodiesterase Inhibitors: Preparation of a Polycyclic Pyrazolo[3,4-*d*]pyrimidine from an Acylnitroso Diels-Alder Cycloadduct-Derived Aminocyclopentenol," Journal of Organic Chemistry, 2005, 70, 2824-2827.

Kakkar, R. et al., "Inhibition of Bovine Brain Calmodulin-Dependent Cyclic Nucleotide Phosphodiesterase Isozymes by Deprenyl," Life Sciences, 1996, 59 (21), 337-341.

Kakkar, R. et al. "Amantadine: An Antiparkinsonian Agent Inhibits Bovine Brain 60 kDa Calmodulin-Dependent Cyclic Nucleotide Phosphodiesterase Isozyme," Brain Research, 1997, 749 (2), 290-294.

Kakkar, R. et al. "Calmodulin-dependent Cyclic Nucleotide Phosphodiesterase (PDE1)," CMLS Cellular and Molecular Life Sciences, 1999, 55 (8-9), 1164-1186.

Klaissle, P. et al., "Physical Activity and Environmental Enrichment Regulate the Generation of Neural Precursors in the Adult Mouse Substantia Nigra in a Dopamine-dependent Manner," BMC Neuroscience, 2012, 13, 132, doi:10.1186/1471-2202-13-132, 15 pages.

Kleppisch, T., "Phosphodiesterases in the Central Nervous System" in cGMP: Generators, Effectors and Therapuetic Implications, Handbook of Experimental Pharmacology, 191, Schmidt, H. et al., Eds., Springer-Verlag, Berlin, 2009, pp. 71-92.

Laddha, S. et al., "A New Therapeutic Approach in Parkinson's Disease: Some Novel Quinazoline Derivatives as Dual Selective

(56) References Cited

OTHER PUBLICATIONS

Phosphodiesterase 1 Inhibitors and Anti-inflammatory Agents" Bioorganic & Medicinal Chemistry, 2009, 17 (19), 6796-6802.

Lundqvist, T. et al., "Exploitation of Structural and Regulatory Diversity in Glutamate Racemases," Nature, 2007, 447, 817-822.

Mani, S. et al., "Requirement for DARPP-32 in Progesterone Facilitated Sexual Receptivity in Female Rats and Mice," Science, 2000, 287, 1053-1056.

Medina, a., "Therapeutic Utility of Phosphodiesterase Type 1 Inhibitors in Neurological Conditions," Frontiers in Neuroscience, 2011, 5, 21, 6 pages.

Murray, F. et al., "Expression and Activity of cAMP Phosphodiesterase Isoforms in Pulmonary Artery Smooth Muscle Cells from Patients with Pulmonary Hypertension: Role for PDE1," American Journal of Physiology, Lung Cellular and Molecular Physiology, 2007, 292, L294-L303.

Murray, T. et al., "LY503430, A Novel α-Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, 2003, 306 (2), 752-762.

Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, 2010, 114, 6-16.

Noguchi, M. et al., "A Facile Preparation of 7-(Substituted Amino-)-6H-pyrrolo[3,4-d]-pyrimidine Derivatives," Bulletin of the Chemical Society of Japan, 1989, 62 (9), 3043-3045.

Park, E, et al., "Traumatic Brain Injury: Can the Consequences Be Stopped?" CMAJ, 2008, 178 (9), 1163-1170.

Polli, J. et al., "Expression of a Calmodulin-dependent Phosphodiesterase Isoform (PDE1B1) Correlates With Brain Regions Having Extensive Dopaminergic Innervation," The Journal of Neuroscience, 1994, 14 (3), 1251-1261.

Porsolt, R. et al., "Depression: A New Animal Model Sensitive to Antidepressant Treatments," Nature, 1977, 266, 730-732.

Poulsen, S. et al., "High-Pressure Synthesis of Enantiomerically Pure C-6 Substituted Pyrazolo[3,4-d]pyrimidines," Biorganic & Medicinal Chemistry Letters, 2001, 11, 191-193.

Prickaerts, J. et al., "Possible Role of Nitric Oxide-Cyclic GMP Pathway in Object Recognition Memory: Effects of 7-Nitroindazole and Zaprinast," European Journal of Pharmacology, 1997, 337, 125-136.

Reed, T. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 2002, 22 (12), 5188-5197.

Rybalkin, S. et al., "Cyclic GMP Phosphodiesterases and Regulation of Smooth Muscle Function," Circulation Research, 2003, 93, 280-291.

Schmidt, C., "Phosphodiesterase Inhibitors as Potential Cognition Enhancing Agents," Current Topics in Medicinal Chemistry, 2010, 10 (2), 222-230.

Sharma, R. et al., "Regulation of Calmodulin-Stimulated Cyclic Nucleotide Phosphodiesterase (PDE1): Review," International Journal of Molecular Medicine, 2006, 18, 95-105.

Shimizu, K. et al., "Calmodulin-Dependent Cyclic Nucleotide Phosphodiesterase (PDE1) Is a Pharmacological Target of Differentiation-Inducing Factor-1, an Antitumor Agent Isolated from *Dictyostelium*," Cancer Research, 2004, 64, 2568-2571.

Shook, B. et al., "Design and Characterization of Optimized Adenosine $A_{2A}/A_1$ Receptor Antagonists for the Treatment of Parkinson's Disease," Journal of Medicinal Chemistry, doi:10.1021/jm201640m, 2012, 47 pages.

Turko, I. et al , "Inhibition of Cyclic GMP-Binding Cyclic GMP-Specific Phosphodiesterase (Type 5) by Sildenafil and Related Compounds," Molecular Pharmacology, 1999, 56, 124-130.

Ungerstedt, U. et al., "Quantitative Recording of Rotational Behavior in Rats After 6-Hydroxy-dopamine Lesions of the Nigrostriatal Dopamine System," Brain Research, 1970, 24, 485-493.

Ungerstedt, U., "Stereotaxic Mapping of the Monoamine Pathways in the Rat Brain*," Acta Physiologica Scandinavica, Supplementum 367, 1971, 1-48.

Vatter, S. et al., "Differential Phosphodiesterase Expression and Cytosolic $Ca^{2+}$ in Human CNS Tumour Cells and in Non-Malignant and Malignant Cells of Rat Origin," Journal of Neurochemistry, 2005, 93, 321-329.

Wolff, M. Ed., Burger's Medicinal Chemistry and Drug Discovery, Fifth Edition, vol. I: Principles and Practice, John Wiley & Sons, New York, 1995, 975-977.

Xia, Y. et al., "Synthesis and Evaluation of Polycyclic Pyrazolo[3,4-d]pyrimidines as PDE1 and PDE5 cGMP Phosphodiesterase Inhibitors," Journal of Medicinal Chemistry, 1997, 40, 4372-4377.

Applicant-Initiated Interview Summary mailed Sep. 13, 2012, Response to 312 Communication mailed Aug. 24, 2012, Applicant-Initiated Interview Summary mailed Jul. 23, 2012, Examiner-Initiated Interview Summary mailed Apr. 18, 2012, Applicant-Initiated Interview Summary mailed Apr. 18, 2012, Notice of Allowance and Fee(s) Due mailed Apr. 18, 2012, Final Office Action mailed Jan. 31, 2012, Non-Final Office Action mailed Aug. 16, 2011, Advisory Action mailed Mar. 30, 2010, Final Office Action mailed Dec. 30, 2009, Non-Final Office Action mailed Aug. 18, 2009, in U.S. Appl. No. 11/916,761, 74 pages.

Requirement for Restriction/Election mailed May 28, 2009, in U.S. Appl. No. 11/916,761, 9 pages.

Final Office Action mailed Apr. 23, 2014, Non-Final Office Action mailed Nov. 4, 2013, in U.S. Appl. No. 13/552,381, 14 pages.

Applicant-Initiated Interview Summary mailed Apr. 26, 2012, Notice of Allowance and Fee(s) Due mailed Apr. 26, 2012, Final Office Action mailed Mar. 27, 2012, Non-Final Office Action mailed Nov. 29, 2011, in U.S. Appl. No. 12/746,236, 27 pages.

Advisory Action mailed Jan. 14, 2014, Final Office Action mailed Oct. 24, 2013, and Non-Final Office Action mailed Apr. 30, 2013, for U.S. Appl. No. 13/486,264, 29 pages.

Notice of Allowance and Fee(s) Due mailed Apr. 25, 2014, Applicant-Initiated Interview Summary mailed Jan. 27, 2014, for U.S. Appl. No. 13/486,264, 12 pages.

Pardo, C. et al., "Synthesis of 1-(p-Nitrobenzyl)Azoles and 1-(pNitrobenzyl)Benzazoles," OPPI Briefs, 2000, 32 (4), 385-390.

\* cited by examiner

ORGANIC COMPOUNDS

This application claims priority to U.S. Provisional Application No. 61/788,551, filed on Mar. 15, 2013, the contents of which are hereby incorporated by reference.

TECHNICAL FIELD

The present invention relates to PDE1 inhibitory compounds of Formula I as described below, processes for their production, their use as pharmaceuticals and pharmaceutical compositions comprising them. These compounds are useful e.g., in the treatment of diseases involving disorders of the dopamine D1 receptor intracellular pathway, such as, among others, Parkinson's disease, depression, narcolepsy, psychosis, damage to cognitive function, e.g., in schizophrenia, or disorders that may be ameliorated through enhanced progesterone-signaling pathway, e.g., female sexual dysfunction.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate both the calcium and cyclic nucleotide (e.g. cAMP and cGMP) signaling pathways. The three known CaM-PDE genes, PDE1A, PDE1B, and PDE1C, are all expressed in human central nervous system tissue. PDE1A is expressed in the brain with high levels in the CA1 to CA3 layers of the hippocampus and cerebellum and at a low level in the striatum. PDE1B is predominately expressed in the striatum, dentate gyms, olfactory tract and in the prefrontal cortex colocalized with the dopamine D1 receptor. Its expression generally correlates with brain regions having high levels of dopaminergic innervation. Although PDE1B is primarily expressed in the central nervous system, it is present in neutrophils. PDE1C is more ubiquitously expressed in the brain and is expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of adenylate cyclases, resulting in increased cAMP. This cyclic nucleotide in turn activates protein kinase A (PKA; cAMP-dependent protein kinase). Production of cGMP is known to occur in tissues involved in cognitive function through various stimulations such as nitric oxide production induced by high intra-cellular calcium levels and to subsequently activate protein kinase G (PKG; cGMP-dependent protein kinase). PKG and PKA phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphates-1 (PP-1), thereby increasing the state of phosphorylation of substrate proteins such as progesterone receptor (PR), leading to induction of physiologic responses. D1 receptor signaling is disrupted in schizophrenia, contributing to cognitive impairment in the disease. The role of cAMP and cGMP in cognitive function has been well established in animal studies. Studies in rodents also have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity that is a consequence of D2 receptor-mediated increases in intra-cellular calcium. Chronic elevation in intracellular calcium levels is linked to cell death in numerous disorders, particularly in neurodegenerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment such as cognitive impairment associated with schizophrenia. PDE1 inhibitors are also useful in diseases that may be alleviated by the enhancement of progesterone-signaling such as female sexual dysfunction.

There is thus a need for compounds that selectively inhibit PDE1 activity.

SUMMARY OF THE INVENTION

The invention provides a compound of Formula I:

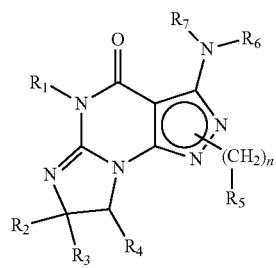

Formula I wherein
(i) $R_1$ is H or $C_{1-4}$ alkyl (e.g., methyl or ethyl);
(ii) $R_2$ and $R_3$ are independently H or $C_{1-6}$ alkyl (e.g., methyl or ethyl);
(iii) $R_4$ is H or $C_{1-4}$ alkyl (e.g., methyl or ethyl);
(iv) $R_5$ is aryl (e.g., phenyl) optionally substituted with one or more groups independently selected from —C(=O)—$C_{1-6}$ alkyl (e.g., —C(=O)—$CH_3$) and $C_{1-6}$-hydroxyalkyl (e.g., 1-hydroxyethyl);
(v) $R_6$ and $R_7$ are independently H or aryl (e.g., phenyl) optionally substituted with one or more groups independently selected from $C_{1-6}$ alkyl (e.g., methyl or ethyl) and halogen (e.g., F or Cl), for example unsubstituted phenyl or phenyl substituted with one or more halogen (e.g., F) or phenyl substituted with one or more $C_{1-6}$ alkyl and one or more halogen or phenyl substituted with one $C_{1-6}$ alkyl and one halogen, for example 4-fluorophenyl or 3,4-difluorophenyl or 4-fluoro-3-methylphenyl; and
(vi) n is 1, 2, 3, or 4,
in free or salt form.

In one embodiment, the compound of Formula I as described above, is a compound of Formula I(i):

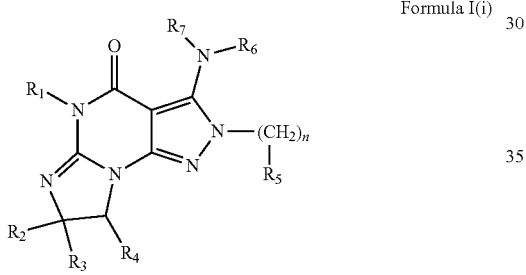

Formula I(i)

wherein
(i) $R_1$ is H or $C_{1-4}$ alkyl (e.g., methyl or ethyl);
(ii) $R_2$ and $R_3$ are independently H or $C_{1-6}$ alkyl (e.g., methyl or ethyl);
(iii) $R_4$ is H or $C_{1-4}$ alkyl (e.g., methyl or ethyl);
(iv) $R_5$ is aryl (e.g., phenyl) optionally substituted with one or more groups independently selected from —C(=O)—$C_{1-6}$ alkyl (e.g., —C(=O)—$CH_3$) and $C_{1-6}$-hydroxyalkyl (e.g., 1-hydroxyethyl);
(v) $R_6$ and $R_7$ are independently H or aryl (e.g., phenyl) optionally substituted with one or more groups independently selected from $C_{1-6}$ alkyl (e.g., methyl or ethyl) and halogen (e.g., F or Cl), for example unsubstituted phenyl or phenyl substituted with one or more halogen (e.g., F) or phenyl substituted with one or more $C_{1-6}$ alkyl and one or more halogen or phenyl substituted with one $C_{1-6}$ alkyl and one halogen, for example 4-fluorophenyl or 3,4-difluorophenyl or 4-fluoro-3-methylphenyl; and
(vi) n is 1, 2, 3, or 4,
in free or salt form.

In another embodiment, the compound of Formula I as described above, is a compound of Formula I(ii):

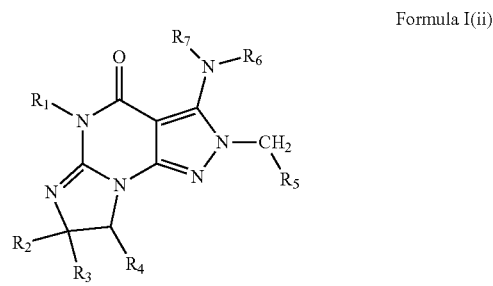

Formula I(ii)

wherein
(i) $R_1$ is H or $C_{1-4}$ alkyl (e.g., methyl or ethyl);
(ii) $R_2$ and $R_3$ are independently H or $C_{1-6}$ alkyl (e.g., methyl or ethyl);
(iii) $R_4$ is H or $C_{1-4}$ alkyl (e.g., methyl or ethyl);
(iv) $R_5$ is aryl (e.g., phenyl) optionally substituted with one or more groups independently selected from —C(=O)—$C_{1-6}$ alkyl (e.g., —C(=O)—$CH_3$) and $C_{1-6}$-hydroxyalkyl (e.g., 1-hydroxyethyl); and
(v) $R_6$ and $R_7$ are independently H or aryl (e.g., phenyl) optionally substituted with one or more groups independently selected from $C_{1-6}$ alkyl (e.g., methyl or ethyl) and halogen (e.g., F or Cl), for example unsubstituted phenyl or phenyl substituted with one or more halogen (e.g., F) or phenyl substituted with one or more $C_{1-6}$ alkyl and one or more halogen or phenyl substituted with one $C_{1-6}$ alkyl and one halogen, for example 4-fluorophenyl or 3,4-difluorophenyl or 4-fluoro-3-methylphenyl,
in free or salt form.

The invention further provides compounds of Formula I, I(i), and I(ii) as follows:
1.1 Formula I or I(i), wherein n is 1, 2, or 3;
1.2 Formula I or I(i), wherein n is 1 or 2;
1.3 Formula I, wherein n is 1;
1.4 Any of Formulae I, I(i), I(ii), or 1.1-1.3, wherein $R_1$ is H or $C_{1-3}$ alkyl (e.g., methyl);
1.5 Any of Formulae I, I(i), I(ii), or 1.1-1.3, wherein $R_1$ is H;
1.6 Any of Formulae I, I(i), I(ii), or 1.1-1.3, wherein $R_1$ is $C_{1-4}$ alkyl;
1.7 Any of Formulae I, I(i), I(ii), or 1.1-1.3, wherein $R_1$ is methyl;
1.8 Any of Formulae I, I(i), I(ii), or 1.1-1.7, wherein $R_2$ and $R_3$ are independently H or $C_{1-5}$ alkyl (e.g., methyl or ethyl);
1.9 Any of Formulae I, I(i), I(ii), or 1.1-1.7, wherein $R_2$ and $R_3$ are independently H or $C_{1-4}$ alkyl (e.g., methyl);
1.10 Any of Formulae I, I(i), I(ii), or 1.1-1.7, wherein $R_2$ and $R_3$ are both $C_{1-6}$ alkyl (e.g., $C_{1-4}$ alkyl, e.g., methyl);
1.11 Any of Formulae I, I(i), I(ii), or 1.1-1.7, wherein $R_2$ and $R_3$ are both $C_{1-4}$ alkyl (e.g., methyl);
1.12 Any of Formulae I, I(i), I(ii), or 1.1-1.7, wherein $R_2$ and $R_3$ are both methyl;
1.13 Any of Formulae I, I(i), I(ii), or 1.1-1.12, wherein $R_4$ is H or $C_{1-3}$ alkyl (e.g., methyl or ethyl);
1.14 Any of Formulae I, I(i), I(ii), or 1.1-1.12, wherein $R_4$ is H;
1.15 Any of Formulae I, I(i), I(ii) or 1.1-1.14, wherein $R_5$ is aryl (e.g., phenyl) substituted with one or more groups independently selected from —C(=O)—$C_{1-6}$ alkyl (e.g., —C(=O)—$C_{1-4}$ alkyl, e.g., —C(=O)—$CH_3$) and $C_{1-6}$-hydroxyalkyl (e.g., $C_{1-4}$-hydroxyalkyl, e.g., 1.16 Any of Formulae I, I(i), I(ii), or 1.1-1.14, wherein $R_5$ is aryl (e.g., phenyl) substituted with one or more groups independently selected from —C(=O)—$C_{1-4}$ alkyl (e.g., —C(=O)—$CH_3$) and $C_{1-4}$-hydroxyalkyl (e.g., 1-hydroxyethyl), for example substituted with one —C(=O)—$C_{1-4}$ alkyl (e.g., —C(=O)—$CH_3$) or one $C_{1-4}$-hydroxyalkyl (e.g., 1-hydroxyethyl);

1.17 Any of Formulae I, I(i), I(ii), or 1.1-1.14, wherein $R_5$ is phenyl optionally substituted with one or more groups independently selected from —C(=O)—$C_{1-6}$ alkyl (e.g., —C(=O)—$C_{1-4}$ alkyl, e.g., —C(=O)—$CH_3$) and $C_{1-6}$-hydroxyalkyl (e.g., $C_{1-4}$-hydroxyalkyl, e.g., 1-hydroxyethyl);

1.18 Any of Formulae I, I(i), I(ii), or 1.1-1.14, wherein $R_5$ is phenyl substituted with one or more groups independently selected from —C(=O)—$C_{1-6}$ alkyl (e.g., —C(=O)—$C_{1-4}$ alkyl, e.g., —C(=O)—$CH_3$) and $C_{1-6}$-hydroxyalkyl (e.g., $C_{1-4}$-hydroxyalkyl, e.g., 1-hydroxyethyl), for example substituted with one —C(=O)—$C_{1-6}$ alkyl (e.g., —C(=O)—$C_{1-4}$ alkyl, e.g., —C(=O)—$CH_3$) or one $C_{1-6}$-hydroxyalkyl (e.g., $C_{1-4}$-hydroxyalkyl, e.g., 1-hydroxyethyl), for example wherein $R_5$ is 4-acetylphenyl or 4-(1-hydroxyethyl)phenyl;

1.19 Any of Formulae I, I(i), I(ii), or 1.1-1.14, wherein $R_5$ is phenyl substituted with one or more groups independently selected from —C(=O)—$C_{1-4}$ alkyl (e.g., —C(=O)—$CH_3$) and $C_{1-4}$-hydroxyalkyl (e.g., 1-hydroxyethyl), for example substituted with one —C(=O)—$C_{1-4}$ alkyl (e.g., —C(=O)—$CH_3$) or one $C_{1-4}$-hydroxyalkyl (e.g., 1-hydroxyethyl), for example wherein $R_5$ is 4-acetylphenyl or 4-(1-hydroxyethyl)phenyl;

1.20 Any of Formulae I, I(i), I(ii), or 1.1-1.14, wherein $R_5$ is aryl substituted with one or more —C(=O)—$C_{1-6}$ alkyl (e.g., —C(=O)—$C_{1-4}$ alkyl, e.g., —C(=O)—$CH_3$);

1.21 Any of Formulae I, I(i), I(ii), or 1.1-1.14, wherein $R_5$ is aryl substituted with one or more —C(=O)—$C_{1-4}$ alkyl (e.g., —C(=O)—$CH_3$);

1.22 Any of Formulae I, I(i), I(ii), or 1.1-1.14, wherein $R_5$ is aryl substituted with one —C(=O)—$C_{1-6}$ alkyl (e.g., —C(=O)—$C_{1-4}$ alkyl, e.g., —C(=O)—$CH_3$);

1.23 Any of Formulae I, I(i), I(ii), or 1.1-1.14, wherein $R_5$ is aryl substituted with one —C(=O)—$C_{1-4}$ alkyl (e.g., —C(=O)—$CH_3$);

1.24 Any of Formulae I, I(i), I(ii), or 1.1-1.14, wherein $R_5$ is aryl substituted with one —C(=O)—$CH_3$;

1.25 Any of Formulae I, I(i), I(ii), or 1.1-1.14, wherein $R_5$ is aryl substituted with one or more $C_{1-6}$-hydroxyalkyl (e.g., $C_{1-4}$-hydroxyalkyl, e.g., 1-hydroxyethyl);

1.26 Any of Formulae I, I(i), I(ii), or 1.1-1.14, wherein $R_5$ is aryl substituted with one or more $C_{1-4}$-hydroxyalkyl (e.g., 1-hydroxyethyl);

1.27 Any of Formulae I, I(i), I(ii), or 1.1-1.14, wherein $R_5$ is aryl substituted with one $C_{1-6}$-hydroxyalkyl (e.g., $C_{1-4}$-hydroxyalkyl, e.g., 1-hydroxyethyl);

1.28 Any of Formulae I, I(i), I(ii), or 1.1-1.14, wherein $R_5$ is aryl substituted with one $C_{1-4}$-hydroxyalkyl (e.g., 1-hydroxyethyl);

1.29 Any of Formulae I, I(i), I(ii), or 1.1-1.14, wherein $R_5$ is aryl substituted with one 1-hydroxyethyl;

1.30 Any of Formulae I, I(i), I(ii), or 1.1-1.14, wherein $R_5$ is phenyl substituted with one or more —C(=O)—$C_{1-6}$ alkyl (e.g., —C(=O)—$C_{1-4}$ alkyl, e.g., —C(=O)—$CH_3$);

1.31 Any of Formulae I, I(i), I(ii), or 1.1-1.14, wherein $R_5$ is phenyl substituted with one or more —C(=O)—$C_{1-4}$ alkyl (e.g., —C(=O)—$CH_3$);

1.32 Any of Formulae I, I(i), I(ii), or 1.1-1.14, wherein $R_5$ is phenyl substituted with one —C(=O)—$C_{1-6}$ alkyl (e.g., —C(=O)—$C_{1-4}$ alkyl, e.g., —C(=O)—$CH_3$);

1.33 Any of Formulae I, I(i), I(ii), or 1.1-1.14, wherein $R_5$ is phenyl substituted with one —C(=O)—$C_{1-4}$ alkyl (e.g., —C(=O)—$CH_3$);

1.34 Any of Formulae I, I(i), I(ii), or 1.1-1.14, wherein $R_5$ is phenyl substituted with one —C(=O)—$CH_3$;

1.35 Any of Formulae I, I(i), I(ii), or 1.1-1.14, wherein $R_5$ is 4-acetylphenyl;

1.36 Any of Formulae I, I(i), I(ii), or 1.1-1.14, wherein $R_5$ is phenyl substituted with one or more $C_{1-6}$-hydroxyalkyl (e.g., $C_{1-4}$-hydroxyalkyl, e.g., 1-hydroxyethyl);

1.37 Any of Formulae I, I(i), I(ii), or 1.1-1.14, wherein $R_5$ is phenyl substituted with one or more $C_{1-4}$-hydroxyalkyl (e.g., 1-hydroxyethyl);

1.38 Any of Formulae I, I(i), I(ii), or 1.1-1.14, wherein $R_5$ is phenyl substituted with one $C_{1-6}$-hydroxyalkyl (e.g., $C_{1-4}$-hydroxyalkyl, e.g., 1-hydroxyethyl);

1.39 Any of Formulae I, I(i), I(ii), or 1.1-1.14, wherein $R_5$ is phenyl substituted with one $C_{1-4}$-hydroxyalkyl (e.g., 1-hydroxyethyl);

1.40 Any of Formulae I, I(i), I(ii) or 1.1-1.14, wherein $R_5$ is phenyl substituted with one 1-hydroxyethyl;

1.41 Any of Formulae I, I(i), I(ii) or 1.1-1.14, wherein $R_5$ is 4-(1-hydroxyethyl)phenyl;

1.42 Any of Formulae I, I(i), I(ii) or 1.1-1.41, wherein $R_6$ and $R_7$ are independently H or aryl (e.g., phenyl) substituted with one or more groups independently selected from $C_{1-6}$ alkyl (e.g., $C_{1-4}$ alkyl, e.g., methyl or ethyl) and halogen (e.g., F or Cl), for example phenyl substituted with one or more (e.g., two) halogen (e.g., F) or phenyl substituted with one or more $C_{1-6}$ alkyl (e.g., $C_{1-4}$ alkyl, e.g., methyl) and one or more halogen (e.g., F) or phenyl substituted with one $C_{1-6}$ alkyl (e.g., $C_{1-4}$ alkyl, e.g., methyl) and one halogen (e.g., F), for example 4-fluorophenyl or 3,4-difluorophenyl or 4-fluoro-3-methylphenyl;

1.43 Any of Formulae I, I(i), I(ii), or 1.1-1.41, wherein $R_7$ is H and $R_6$ is aryl (e.g., phenyl) substituted with one or more groups independently selected from $C_{1-6}$ alkyl (e.g., $C_{1-4}$ alkyl, e.g., methyl) and halogen (e.g., F or Cl), for example $R_6$ is phenyl substituted with one or more (e.g., two) halogen (e.g., F) or phenyl substituted with one $C_{1-6}$ alkyl (e.g., $C_{1-4}$ alkyl, e.g., methyl) and one halogen (e.g., F), for example wherein $R_6$ is 4-fluorophenyl or 3,4-difluorophenyl or 4-fluoro-3-methylphenyl;

1.44 Formulae I, I(i), I(ii), or 1.1-1.41, wherein $R_7$ is H and $R_6$ is aryl (e.g., phenyl) substituted with one or more groups independently selected from $C_{1-4}$ alkyl (e.g., methyl) and halogen (e.g., F), for example $R_6$ is phenyl substituted with one or more (e.g., two) halogen (e.g., F) or phenyl substituted with one $C_{1-4}$ alkyl (e.g., methyl) and one halogen (e.g., F), for example wherein $R_6$ is 4-fluorophenyl or 3,4-difluorophenyl or 4-fluoro-3-methylphenyl;

1.45 Any of Formulae I, I(i), I(ii), or 1.1-1.41, wherein $R_7$ is H and $R_6$ is aryl (e.g., phenyl) substituted with one or more halogen (e.g., F);

1.46 Any of Formulae I, I(i), I(ii), or 1.1-1.41, wherein $R_7$ is H and $R_6$ is aryl (e.g., phenyl) substituted with two halogens (e.g., F);

1.47 Any of Formulae I, I(i), I(ii), or 1.1-1.41, wherein $R_7$ is H and $R_6$ is aryl (e.g., phenyl) substituted with one halogen (e.g., F);

1.48 Any of Formulae I, I(i), I(ii), or 1.1-1.41, wherein $R_7$ is H and $R_6$ is aryl (e.g., phenyl) substituted with two F;

1.49 Any of Formulae I, I(i), I(ii), or 1.1-1.41, wherein $R_7$ is H and $R_6$ is aryl (e.g., phenyl) substituted with one F;

1.50 Any of Formulae I, I(i), I(ii), or 1.1-1.41, wherein $R_7$ is H and $R_6$ is aryl (e.g., phenyl) substituted with one or more $C_{1-6}$ alkyl (e.g., $C_{1-4}$ alkyl, e.g., methyl) and one or more halogen (e.g., F);

1.51 Any of Formulae I, I(i), I(ii), or 1.1-1.41, wherein $R_7$ is H and $R_6$ is aryl (e.g., phenyl) substituted with one or more $C_{1-4}$ alkyl (e.g., methyl) and one or more halogen (e.g., F);

1.52 Any of Formulae I, I(i), I(ii), or 1.1-1.41, wherein $R_7$ is H and $R_6$ is aryl (e.g., phenyl) substituted with one $C_{1-6}$ alkyl (e.g., $C_{1-4}$ alkyl, e.g., methyl) and one halogen (e.g., F);

1.53 Any of Formulae I, I(i), I(ii), or 1.1-1.41, wherein $R_7$ is H and $R_6$ is aryl (e.g., phenyl) substituted with one $C_{1-4}$ alkyl (e.g., methyl) and one halogen (e.g., F);

1.54 Any of Formulae I, I(i), I(ii), or 1.1-1.41, wherein $R_7$ is H and $R_6$ is aryl (e.g., phenyl) substituted with one methyl and one F;

1.55 Any of Formulae I, I(i), I(ii), or 1.1-1.41, wherein $R_7$ is H and $R_6$ is phenyl substituted with one or more halogen (e.g., F);

1.56 Any of Formulae I, I(i), I(ii), or 1.1-1.41, wherein $R_7$ is H and $R_6$ is phenyl substituted with two halogens (e.g., F);

1.57 Any of Formulae I, I(i), I(ii), or 1.1-1.41, wherein $R_7$ is H and $R_6$ is phenyl substituted with one halogen (e.g., F);

1.58 Any of Formulae I, I(i), I(ii), or 1.1-1.41, wherein $R_6$ is phenyl substituted with two F;

1.59 Any of Formulae I, I(i), I(ii), or 1.1-1.41, wherein $R_7$ is H and $R_6$ is phenyl substituted with one F;

1.60 Any of Formulae I, I(i), I(ii), or 1.1-1.41, wherein $R_7$ is H and $R_6$ is 3,4-difluorophenyl;

1.61 Any of Formulae I, I(i), I(ii), or 1.1-1.41, wherein $R_7$ is H and $R_6$ is 4-fluorophenyl;

1.62 Any of Formulae I, I(i), I(ii), or 1.1-1.41, wherein $R_7$ is H and $R_6$ is phenyl substituted with one or more $C_{1-6}$ alkyl (e.g., $C_{1-4}$ alkyl, e.g., methyl) and one or more halogen (e.g., F);

1.63 Any of Formulae I, I(i), I(ii), or 1.1-1.41, wherein $R_7$ is H and $R_6$ is phenyl substituted with one or more $C_{1-4}$ alkyl (e.g., methyl) and one or more halogen (e.g., F);

1.64 Any of Formulae I, I(i), I(ii), or 1.1-1.41, wherein $R_7$ is H and $R_6$ is phenyl substituted with one $C_{1-6}$ alkyl (e.g., $C_{1-4}$ alkyl, e.g., methyl) and one halogen (e.g., F);

1.65 Any of Formula I, I(i), I(ii), or 1.1-1.41, wherein $R_7$ is H and $R_6$ is phenyl substituted with one $C_{1-4}$ alkyl (e.g., methyl) and one halogen (e.g., F);

1.66 Any of Formulae I, I(i), I(ii), or 1.1-1.41, wherein $R_7$ is H and $R_6$ is phenyl substituted with one methyl and one F;

1.67 Any of Formulae I, I(i), I(ii), or 1.1-1.41, wherein $R_7$ is H and $R_6$ is 4-fluoro-3-methylphenyl;

1.68 Any of Formulae I, I(i), or I(ii), wherein $R_1$ is $C_{1-4}$ alkyl (e.g., methyl); $R_2$ and $R_3$ are independently $C_{1-6}$ alkyl (e.g., $C_{1-4}$ alkyl, e.g., methyl); $R_4$ is H; $R_5$ is aryl (e.g., phenyl) substituted with one or more groups independently selected from —C(=O)—$C_{1-6}$ alkyl (e.g., —C(=O)—$C_{1-4}$ e.g., —C(=O)—$CH_3$) and $C_{1-6}$-hydroxyalkyl (e.g., $C_{1-4}$-hydroxyalkyl, e.g., 1-hydroxyethyl), for example $R_5$ is aryl (e.g., phenyl) substituted with one —C(=O)—$C_{1-6}$ alkyl (e.g., —C(=O)—$C_{1-4}$ alkyl, e.g., —C(=O)—$CH_3$) or one $C_{1-6}$-hydroxyalkyl (e.g., $C_{1-4}$-hydroxyalkyl, e.g., 1-hydroxyethyl), for example wherein $R_5$ is 4-acetylphenyl or 4-(1-hydroxyethyl)phenyl; $R_6$ is aryl (e.g., phenyl) substituted with one or more groups independently selected from $C_{1-6}$ alkyl (e.g., $C_{1-4}$ alkyl, e.g., methyl) and halogen (e.g., F), for example phenyl substituted with one or more (e.g., two) halogen (e.g., F) or phenyl substituted with one or more $C_{1-6}$ alkyl (e.g., $C_{1-4}$ alkyl, e.g., methyl) and one or more halogen (e.g., F) or phenyl substituted with one $C_{1-6}$ alkyl (e.g., $C_{1-4}$ alkyl, e.g., methyl) and one halogen (e.g., F), for example wherein $R_6$ is 4-fluorophenyl or 3,4-difluorophenyl or 4-fluoro-3-methylphenyl; and $R^7$ is H, 1.69 Formula I(ii), wherein $R_1$ is $C_{1-4}$ alkyl (e.g., methyl); $R_2$ and $R_3$ are independently $C_{1-6}$ alkyl (e.g., $C_{1-4}$ alkyl, e.g., methyl); $R_4$ is H; $R_5$ is aryl (e.g., phenyl) substituted with one or more groups independently selected from —C(=O)—$C_{1-6}$ alkyl (e.g., —C(=O)—$C_{1-4}$ alkyl, e.g., —C(=O)—$CH_3$) and $C_{1-6}$-hydroxyalkyl (e.g., $C_{1-4}$-hydroxyalkyl, e.g., 1-hydroxyethyl), for example $R_5$ is aryl (e.g., phenyl) substituted with one —C(=O)—$C_{1-6}$ alkyl (e.g., —C(=O)—$C_{1-4}$ alkyl, e.g., —C(=O)—$CH_3$) or one $C_{1-6}$-hydroxyalkyl (e.g., $C_{1-4}$-hydroxyalkyl, e.g., 1-hydroxyethyl), for example wherein $R_5$ is 4-acetylphenyl or 4-(1-hydroxyethyl)phenyl; $R_6$ is aryl (e.g., phenyl) substituted with one or more groups independently selected from $C_{1-6}$ alkyl (e.g., $C_{1-4}$ alkyl, e.g., methyl) and halogen (e.g., F), for example phenyl substituted with one or more (e.g., two) halogen (e.g., F) or phenyl substituted with one or more $C_{1-6}$ alkyl (e.g., $C_{1-4}$ alkyl, e.g., methyl) and one or more halogen (e.g., F) or phenyl substituted with one $C_{1-6}$ alkyl (e.g., $C_{1-4}$ alkyl, e.g., methyl) and one halogen (e.g., F), for example wherein $R_6$ is 4-fluorophenyl or 3,4-difluorophenyl or 4-fluoro-3-methylphenyl; and $R^7$ is H, 1.70 Formula 1.69, wherein $R_2$ and $R_3$ are independently $C_{1-4}$ alkyl (e.g., methyl); $R_5$ is aryl (e.g., phenyl) substituted with one or more groups independently selected from —C(=O)—$C_{1-4}$ alkyl (e.g., —C(=O)—$CH_3$) and $C_{1-4}$-hydroxyalkyl (e.g., 1-hydroxyethyl), for example $R_5$ is aryl (e.g., phenyl) substituted with one —C(=O)—$C_{1-4}$ alkyl (e.g., —C(=O)—$CH_3$) or one $C_{1-4}$-hydroxyalkyl (e.g., 1-hydroxyethyl), for example wherein $R_5$ is 4-acetylphenyl or 4-(1-hydroxyethyl)phenyl; $R_6$ is aryl (e.g., phenyl) substituted with one or more groups independently selected from $C_{1-4}$ alkyl (e.g., methyl) and halogen (e.g., F), for example phenyl substituted with one or more (e.g., two) halogen (e.g., F) or phenyl substituted with one or more $C_{1-4}$ alkyl (e.g., methyl) and one or more halogen (e.g., F) or phenyl substituted with one $C_{1-4}$ alkyl (e.g., methyl) and one halogen (e.g., F), for example wherein $R_6$ is 4-fluorophenyl or 3,4-difluorophenyl or 4-fluoro-3-methylphenyl; and $R^7$ is H, 1.71 Any of the preceding Formulae, wherein $R_5$ is aryl (e.g., phenyl) substituted only in the 4-position with —C(=O)—$C_{1-6}$ alkyl (e.g., —C(=O)—$C_{1-4}$ alkyl, e.g., —C(=O)—$CH_3$) or $C_{1-6}$-hydroxyalkyl (e.g., $C_{1-4}$- hydroxyalkyl, e.g., 1-hydroxyethyl), for example wherein R$_5$ is 4-acetylphenyl or 4-(1-hydroxyethyl)phenyl);

1.72 Any of the preceding Formulae, wherein the compound is selected from:

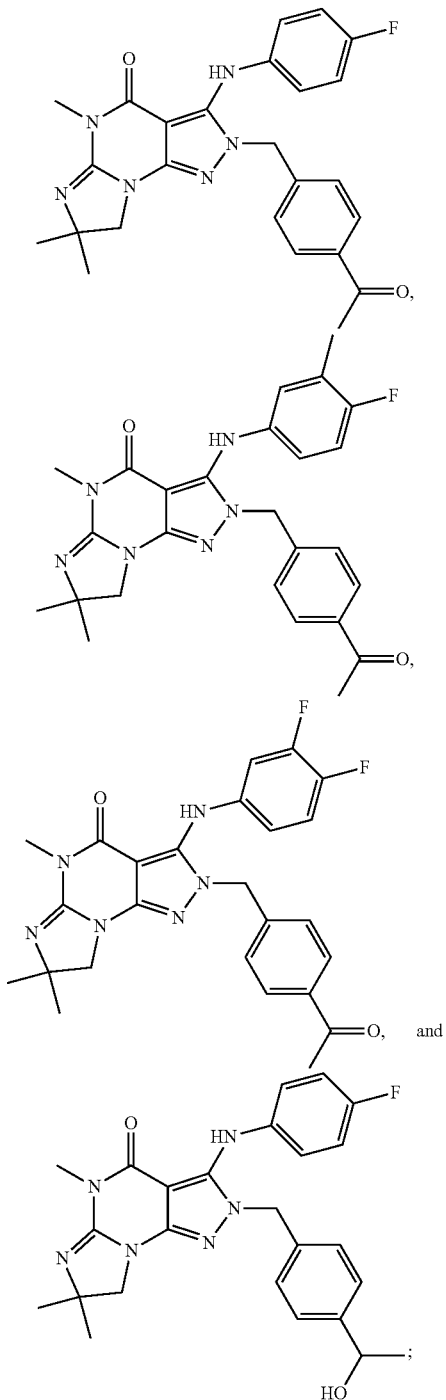

1.73 Any of the preceding Formulae wherein the compounds inhibit phosphodiesterase-mediated (e.g., PDE1-mediated) hydrolysis of cGMP, e.g., with an IC$_{50}$ of less than 1 μM, preferably less than 500 nm, more preferably less than 50 nM, still more preferably less than 10 nM, most preferably less than or equal to 5 nM in an immobilized-metal affinity particle reagent PDE assay, for example, as described in Example 5, in free or salt form.

If not otherwise specified or clear from context, the following terms herein have the following meanings:

(a) "Alkyl" as used herein is a saturated or unsaturated hydrocarbon moiety, preferably saturated, preferably having one to six carbon atoms, preferably having one to four carbon atoms, which may be linear or branched, and may be optionally mono-, di- or tri-substituted, e.g., with halogen (e.g., Cl or F) or carboxy.

(b) "Hydroxyalkyl" as used herein is a saturated hydrocarbon moiety, preferably having one to six carbon atoms, preferably having one to four carbon atoms, which may be linear or branched, and is mono-, di- or tri-substituted with hydroxy.

(c) "Haloalkyl" as used herein is a saturated hydrocarbon moiety, preferably having one to six carbon atoms, preferably having one to four carbon atoms, which may be linear or branched, and is mono-, di- or tri-substituted with halogen. For di- or tri-substituted haloalkyl, the halogens may be the same (e.g., dichloromethyl) or different (e.g., chlorofluoromethyl).

(d) "Aryl" as used herein is a mono or bicyclic aromatic hydrocarbon, preferably phenyl, which may be optionally substituted, e.g., optionally substituted with one or more groups independently selected from C$_{1-6}$ alkyl (e.g., methyl), halogen (e.g., Cl or F), C$_{1-6}$-haloalkyl (e.g., trifluoromethyl), hydroxy, and carboxy. In some embodiments, aryl, in addition to being substituted with the groups disclosed herein, is further substituted with an aryl or a heteroaryl to form, e.g., biphenyl or pyridylphenyl.

(e) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., optionally substituted with one or more groups independently selected from C$_{1-6}$ alkyl (e.g., methyl), halogen (e.g., Cl or F), C$_{1-6}$-haloalkyl (e.g., trifluoromethyl), hydroxy, and carboxy.

(f) "Hydroxy" as used herein is —OH.

(g) "Carboxy" as used herein is —COOH.

(h) "Halogen" as used herein is F, Cl, Br, or I.

Compounds of the Invention, e.g., compounds of Formulae I, I(i), or I(ii), e.g., any of Formulae 1.1-1.73, may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—C$_{1-4}$alkyl, can hydrolyze in the body to form physiologically hydrolysable alcohol (Compound-OH) on the one hand and acid on the other (e.g., HOC(O)—C$_{1-4}$alkyl). Alternatively, wherein the Compound of the Invention contains a carboxylic acid, for example, Compound-C(O)OH, the acid ester prodrug of such compound, i.e., Compound-C(O)O—C$_{1-4}$alkyl, can hydrolyze to form Compound-C(O)OH and HO—C$_{1-4}$alkyl. As will be appreciated the term thus embraces conventional pharmaceutical prodrug forms.

The invention also provides methods of making the Compounds of the Invention and methods of using the Compounds of the Invention for treatment of diseases and disorders as set forth below (especially treatment of diseases characterized by reduced dopamine D1 receptor signaling activity, such as Parkinson's disease, Tourette's Syndrome, autism, fragile X syndrome, ADHD, restless leg syndrome, depression, cognitive impairment, e.g., cognitive impairment of schizophrenia, narcolepsy and diseases that may be alleviated by the enhancement of progesterone-signaling such as female sexual dysfunction or a disease or disorder such as psychosis or glaucoma). This list is not intended to be exhaustive and may include other diseases and disorders as set forth below.

In another embodiment, the invention further provides a pharmaceutical composition comprising a Compound of the Invention, in free, pharmaceutically acceptable salt, or prodrug form, in admixture with a pharmaceutically acceptable diluent or carrier.

DETAILED DESCRIPTION OF THE INVENTION

Methods of Making Compounds of the Invention

The Compounds of the Invention and their pharmaceutically acceptable salts may be made using the methods as described and exemplified herein and by methods similar thereto and by methods known in the chemical art. Such methods include, but are not limited to, those described below. If not commercially available, starting materials for these processes may be made by procedures, which are selected from the chemical art using techniques which are similar or analogous to the synthesis of known compounds. Various starting materials, intermediates and/or Compounds of the Invention may be prepared using methods described or similarly described in WO 2006/133261, WO 2009/075784, WO 2010/065148, WO 2010/065149, and/or WO 2010/065151. All references cited herein are hereby incorporated by reference in their entirety.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}$C, $^{15}$N, $^{18}$O. Alternatively, unstable isotopes, which are radioactive isotopes which contain additional neutrons compared to the abundant nuclides of the same species (i.e., element), e.g., $^{123}$I, $^{131}$I, $^{125}$I, $^{11}$C, $^{18}$F, may replace the corresponding abundant species of I, C, and F. Another example of useful isotope of the compound of the invention is the $^{11}$C isotope. These radio isotopes are useful for radio-imaging and/or pharmacokinetic studies of the compounds of the invention. Methods of making isotopes of PDE1 inhibitors disclosed in WO 2011/043816, the contents of which are incorporated by reference in their entirety, may be used for making the isotopes of the compounds of the current invention.

Melting points are uncorrected and (dec) indicates decomposition. Temperatures are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks. Solvent mixture compositions are given as volume percentages or volume ratios. In cases where the NMR spectra are complex, only diagnostic signals are reported.

Terms and abbreviations:
BOP=benzotriazole-1-yl-oxy-tris-(dimethylamino)-phosphonium hexafluorophosphate
BOC=tert-butyloxycarbonyl,
CAN=ammonium cerium (IV) nitrate,
DBU=1,8-diazabicyclo[5.4.0]undec-7-ene
DIPEA=diisopropylethylamine,
DMF=N,N-dimethylformamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
LDA=lithium diisopropylamide,
LiHMDS=lithium bis(trimethylsilyl)amide,
MeOH=methanol,
NBS=N-bromosuccinimide,
NCS=N-chlorosuccinimide,
NMP=N-methyl-2-pyrrolidone,
NaHCO$_3$=sodium bicarbonate,
NH$_4$OH=ammonium hydroxide,
Pd$_2$(dba)$_3$=tris[dibenzylideneacetone]dipalladium(0)
PMB=p-methoxybenzyl,
POCl$_3$=phosphorous oxychloride,
SOCl$_2$=thionyl chloride,
TFA=trifluoroacetic acid,
TFMSA=trifluoromethanesulfonic acid, and
THF=tetrahydrofuran.

The synthetic methods in this invention are illustrated below. The significances for the R groups are as set forth above for any of Formulae I, I(i), I(ii), or 1.1-1.73 unless otherwise indicated.

In an aspect of the invention, intermediate compounds of formula IIb can be synthesized by reacting a compound of formula IIa with malonic acid and acetic anhydride in acetic acid with heating, e.g., to about 90° C. for about 3 hours, and then cooled:

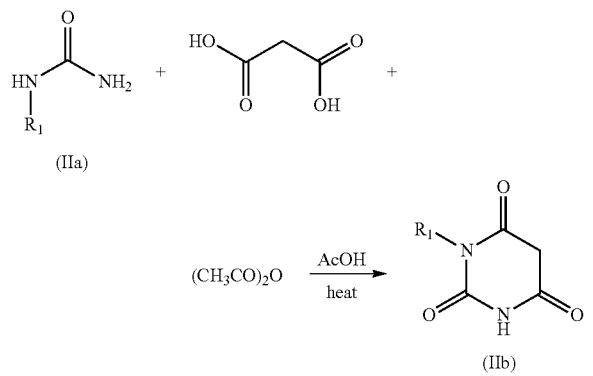

wherein $R_1$ is H or $C_{1-4}$ alkyl, e.g., methyl.

Intermediate IIc can be prepared by for example reacting intermediate IIb with for example a chlorinating compound such as $POCl_3$, sometimes with small amounts of water and heat, e.g., heating to about 80° C. for about 4 hours, and then cooled:

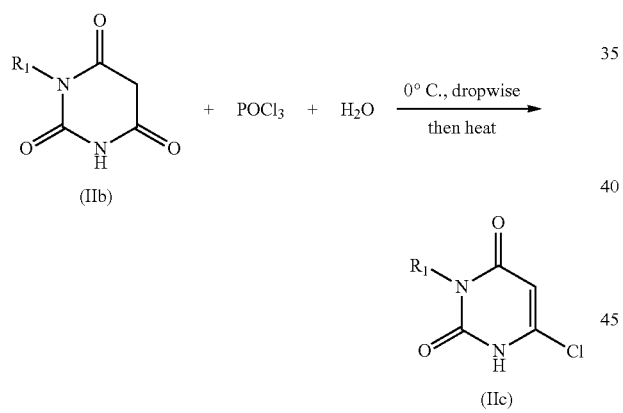

Intermediate IId may be formed by reacting intermediate IIc with for example $P^1$-L in a solvent such as DMF and a base such as $K_2CO_3$, sodium bicarbonate, cesium carbonate, sodium hydroxide, triethylamine, diisopropylethylamine or the like at room temperature or with heating:

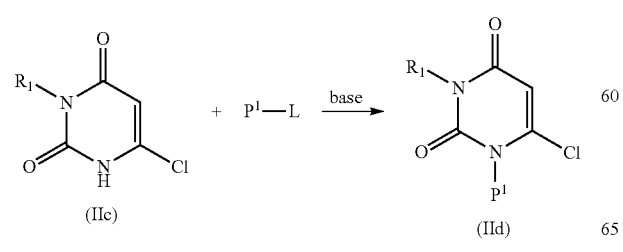

wherein $P^1$ is a protective group [e.g., p-methoxybenzyl group (PMB) or BOC]; L is a leaving group such as a halogen, mesylate, or tosylate. Preferably, $P^1$ is PMB and the base is potassium carbonate.

Intermediate IIe may be prepared by reacting intermediate IId with hydrazine or hydrazine hydrate in a solvent such as methanol and with heating, e.g. refluxed for about 4 hours, and then cooled:

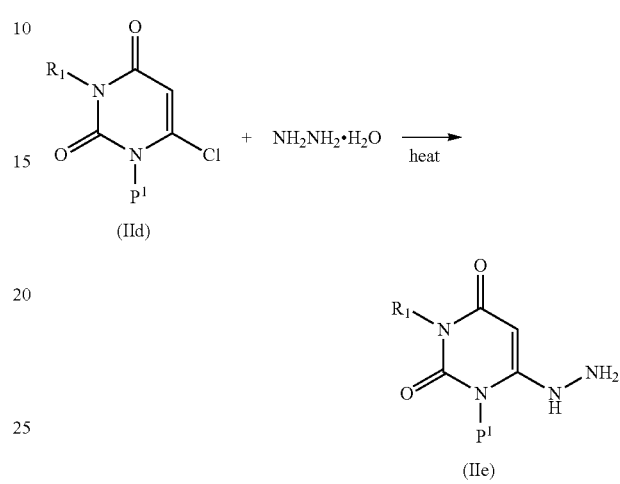

Intermediate IVa may be formed by for example reacting intermediate IIe with $POCl_3$ and DMF:

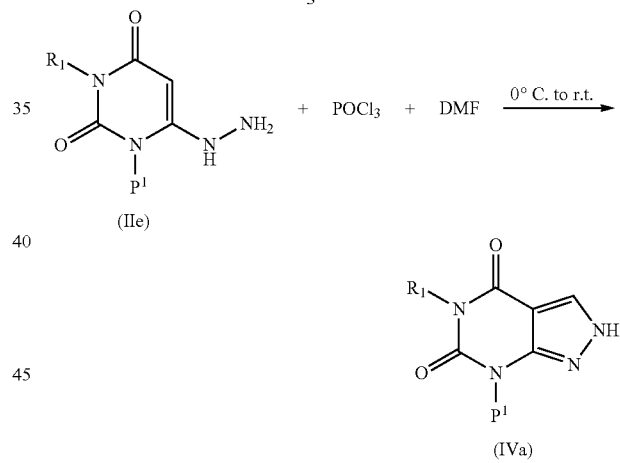

wherein $R_1$ is as defined previously for any of Formulae I, I(i), I(ii), or 1.1-1.73, e.g., such as a methyl group.

Intermediate IVb may be formed by reacting intermediate IVa with for example $F^1$—X in a solvent such as DMF with a base such as $K_2CO_3$ at room temperature (Reaction 1):

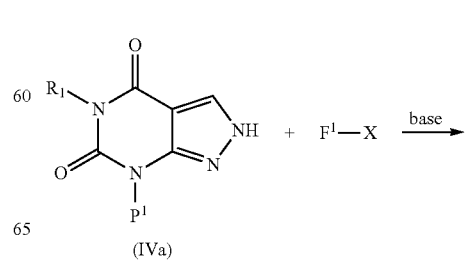

-continued

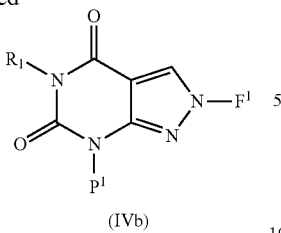

(IVb)

wherein F¹ is for example benzyl substituted with a halogen such as 4-bromobenzyl and X is a halogen (e.g., Br).

Intermediate IVc may be synthesized from intermediate IVb by removing the protective group P¹ with an appropriate method. For example, if P¹ is a PMB group, then it can be removed with CAN or TFA/TFMSA at room temperature (Reaction 2):

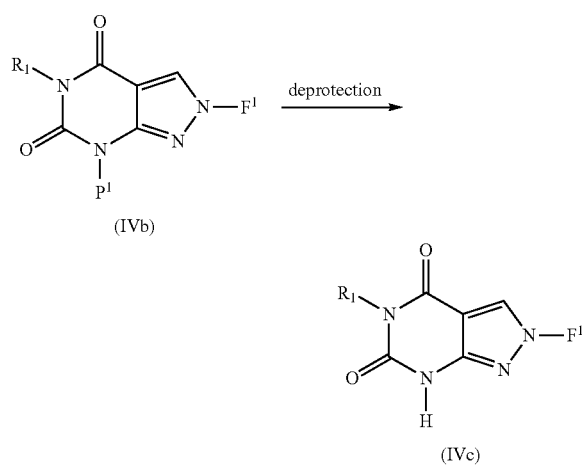

wherein if P¹ is BOC, the compound may be deprotected by using acid such as hydrochloric acid or TFA.

Intermediate IVd can be prepared by reacting intermediate IVc with for example a chlorinating compound such as POCl₃ and optionally with heating, e.g., reflux for about 2 days or more, or heated at 150~200° C. for about 5-10 minutes in a sealed vial with a microwave instrument and then cooled (Reaction 3):

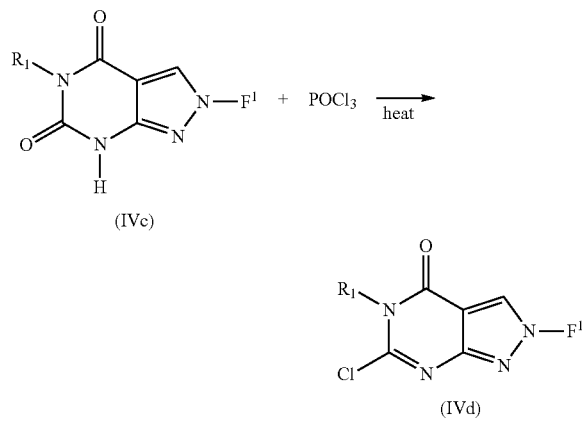

Intermediate IVe can be formed by reacting intermediate IVd with an amino alcohol under basic condition in a solvent such as DMF or NMP and heated then cooled (Reaction 4A):

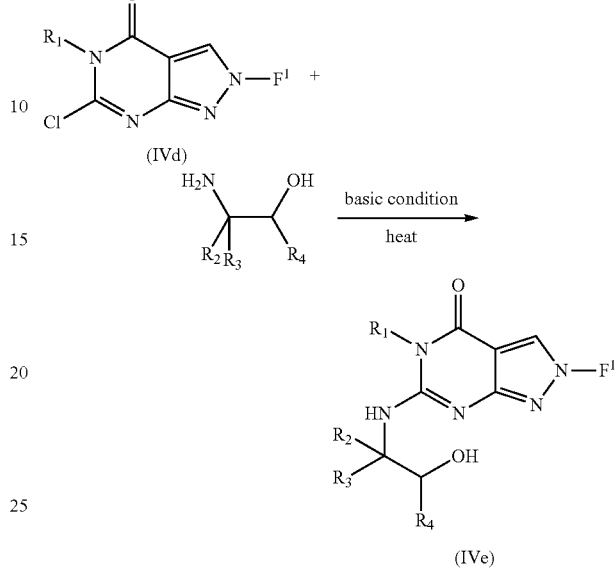

wherein $R_1$, $R_2$, $R_3$, and $R_4$ are as defined previously for any of Formulae I, I(i), I(ii), or 1.1-1.73.

Alternatively, intermediate IVe can be synthesized directly from intermediate IVc by reacting with an amino alcohol and a coupling reagent such as BOP in the presence of a base such as DBU (Reaction 4B):

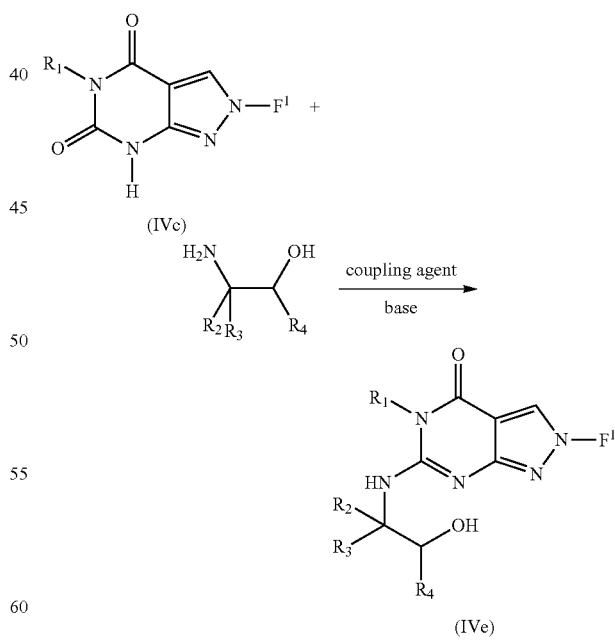

wherein $R_1$, $R_2$, $R_3$, and $R_4$ are as defined previously for any of Formulae I, I(i), I(ii), or 1.1-1.73.

Intermediate IVf may be formed by reacting a compound of IVe with, for example, a dehydrating/halogenating agent such as SOCl$_2$ in a solvent such as CH$_2$Cl$_2$ at room temperature or heated at 35° C. for several hours, and then cooled (Reaction 5):

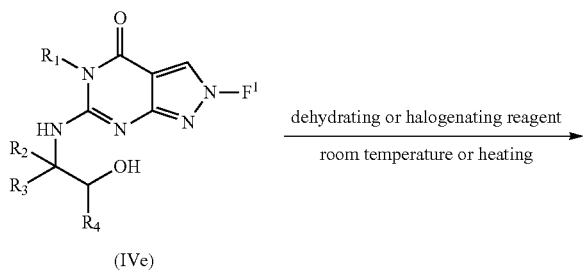

(IVe)

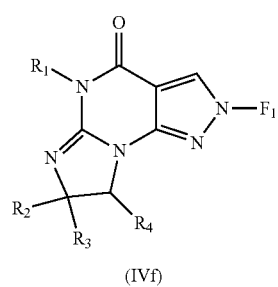

(IVf)

Intermediate IVg may be formed by reacting intermediate IVf with, for example, catalysts such as a copper salt and 2,2,6,6-tetramethylheptane-3,5-dione and a base such as cesium carbonate in a solvent such as NMP with heat for several hours (Reaction 6):

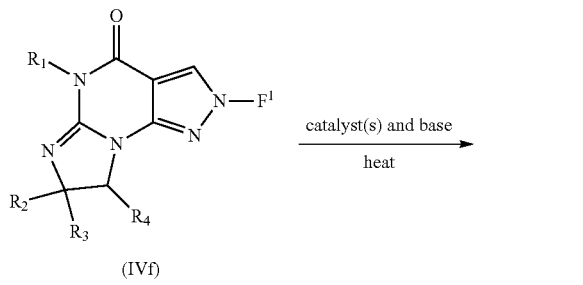

(IVf)

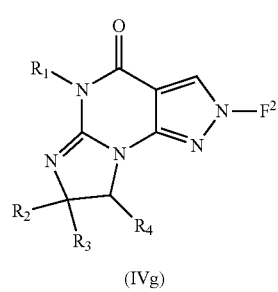

(IVg)

wherein, F$^2$ is a diaryl ether.

Intermediate IVh may be formed by reacting intermediate IVg with, for example, TFA and TFMSA in a solvent such as CH$_2$Cl$_2$ at room temperature (Reaction 7):

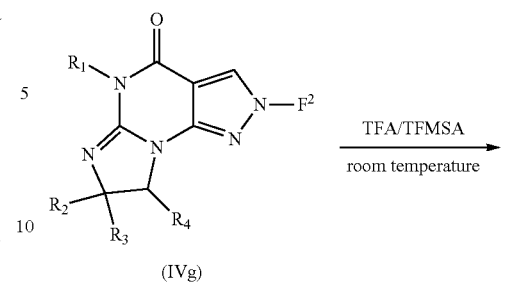

(IVg)

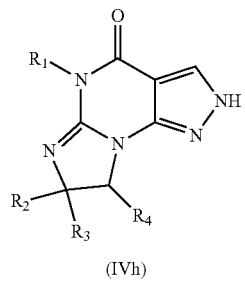

(IVh)

Intermediate IVi may be formed by reacting intermediate IVh with R$_5$—(CH$_2$)$_n$-L in the presence of a base, for example K$_2$CO$_3$, in a solvent such as DMF at room temperature (Reaction 8):

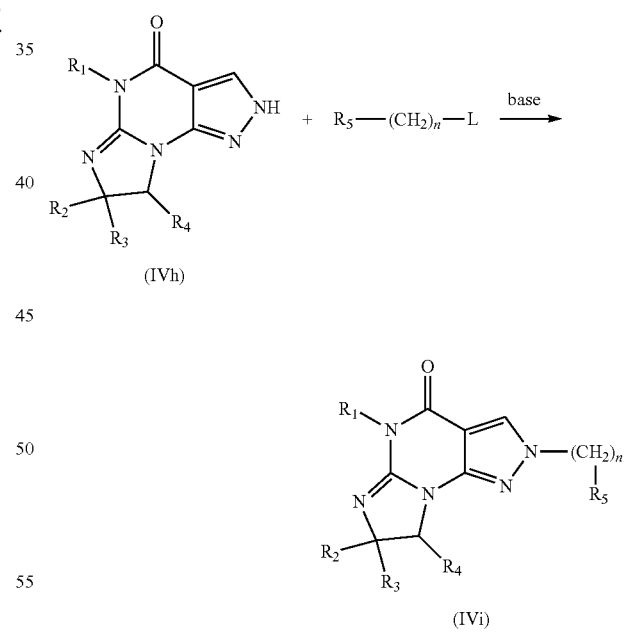

wherein R$_5$ and n are as defined previously for any of Formulae I, I(i), I(ii), or 1.1-1.73 and L is a leaving group such as a halogen (e.g., Br).

Intermediate IVj wherein X is halogen (e.g., Cl) may be formed by reacting intermediate IVi with, for example, a halogenating agent such as hexachloroethane, NCS, NBS, I$_2$ and a base such as LiHMDS in a solvent such as THF at low temperature (Reaction 9):

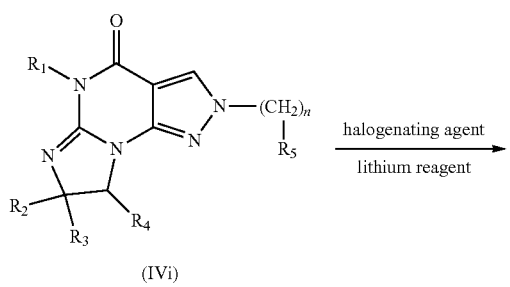

(IVi)

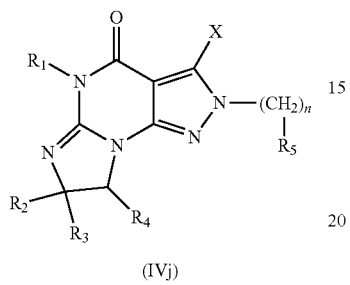

(IVj)

Compounds of the Invention may be formed by reacting intermediate IVj wherein X is halogen (e.g., Cl) with $NHR_6R_7$ and a catalyst with heating (Reaction 10):

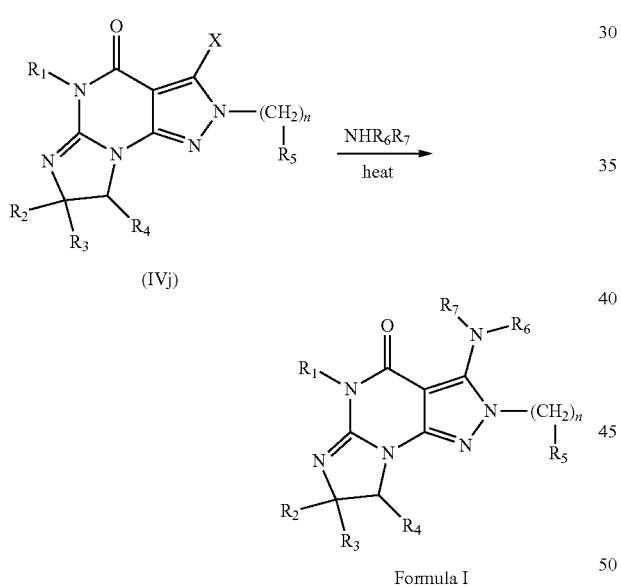

Formula I wherein $R_6$ and $R_7$ are as defined previously for any of Formulae I, I(i), I(ii), or 1.1-1.73.

In another aspect of the invention, intermediate IIf may be prepared by reacting intermediate IIc with hydrazine or hydrazine hydrate in a solvent such as methoxyethanol and refluxed for about 30 minutes and then cooled:

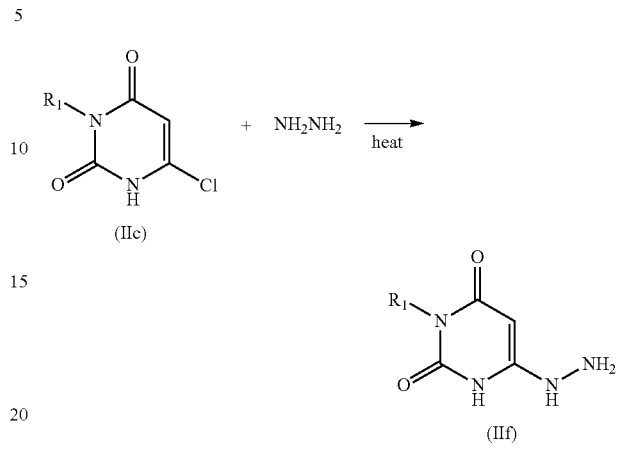

Intermediate Va can be synthesized by reacting a compound of formula IIe with for example an aryl isothiocyanate or isocyanate in a solvent such as DMF and heated at 110° C. for about 2 days and then cooled:

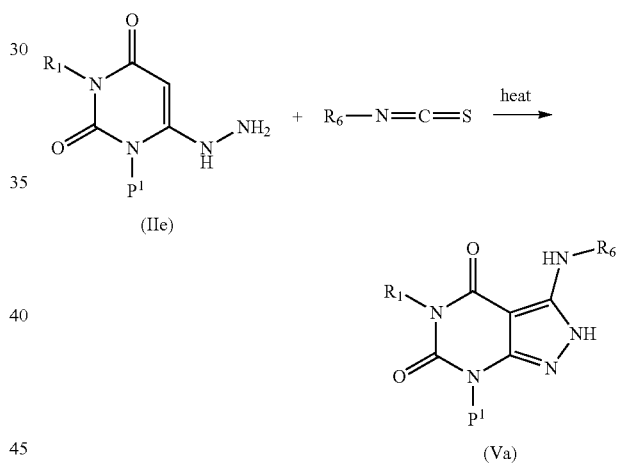

wherein $R_6$ is as defined previously for any of Formulae I, I(i), I(ii), or 1.1-1.73.

Intermediate Vb may be formed by removing the protective group $P^1$ with an appropriate method. For example, if $P^1$ is a PMB group, then it can be removed with $AlCl_3$ or TFA/TFMSA at room temperature. Intermediate Vb may also be prepared directly from a compound of IIf using the similar methods, but the yields are relatively low.

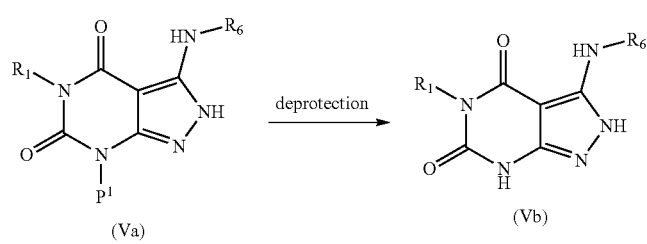

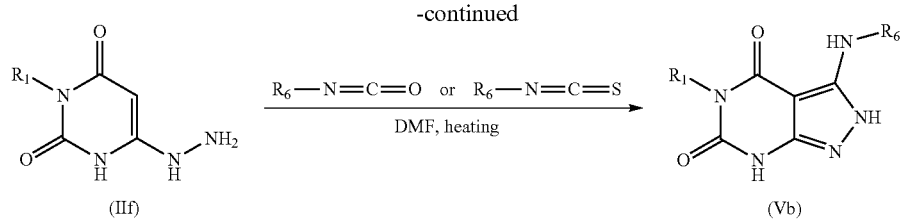

Intermediate Vc can be prepared by for example reacting intermediate Vb with for example a chlorinating compound such as POCl₃. The reaction may be carried out at atmospheric pressure and refluxed for about 2 days or heated at 150~200° C. for about 10 minutes in a sealed vial with a microwave instrument and then cooled (Reaction 11):

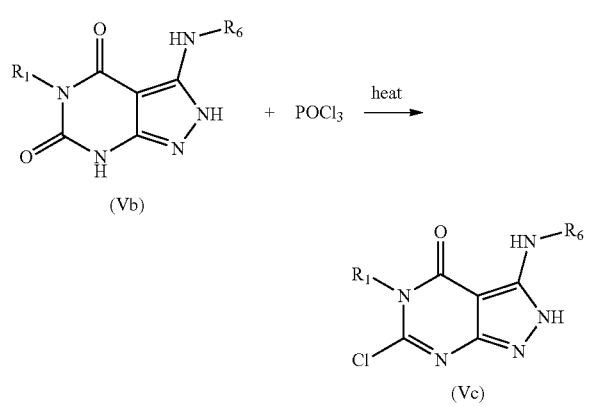

Intermediate Vd can be prepared by reacting intermediate Vc with an amino alcohol under basic condition in a solvent such as DMF. The reaction may be heated overnight and then cooled (Reaction 12):

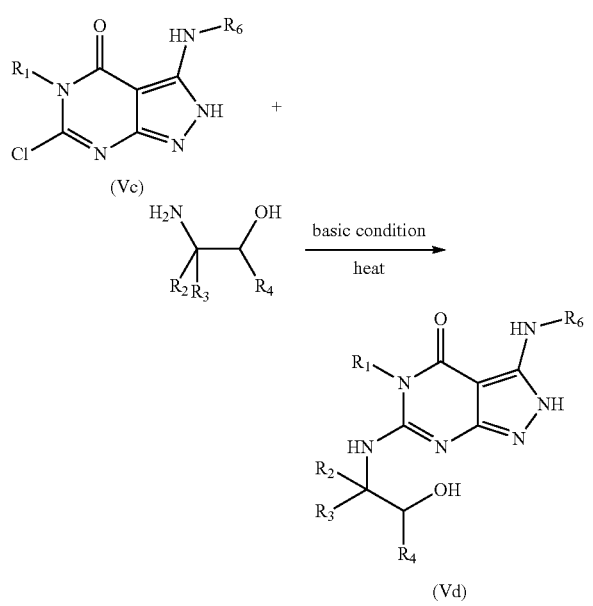

Intermediate Ve can be formed by reacting intermediate Vd with for example a dehydrating agent such as SOCl₂ in a solvent such as CH₂Cl₂ at room temperature overnight or heated at 35° C. for about 4 hours, and then cooled (Reaction 13):

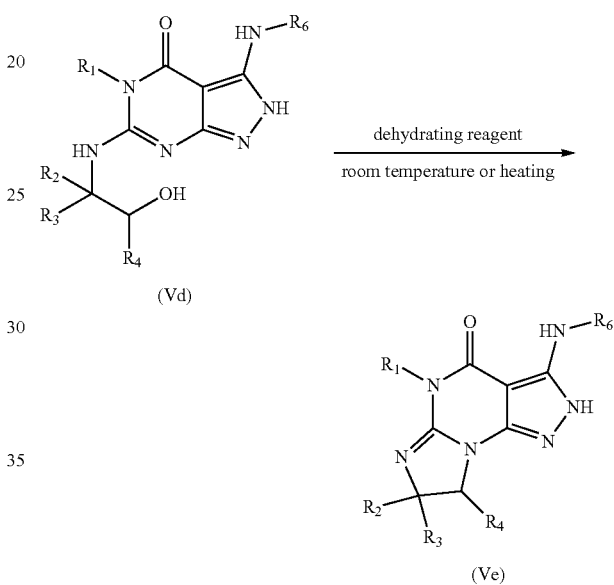

Compounds of the Invention may be formed by reacting intermediate Ve with for example $R_5$—$(CH_2)_n$-L in a solvent such as DMF and a base such as K₂CO₃ at room temperature or with heating (Reaction 14):

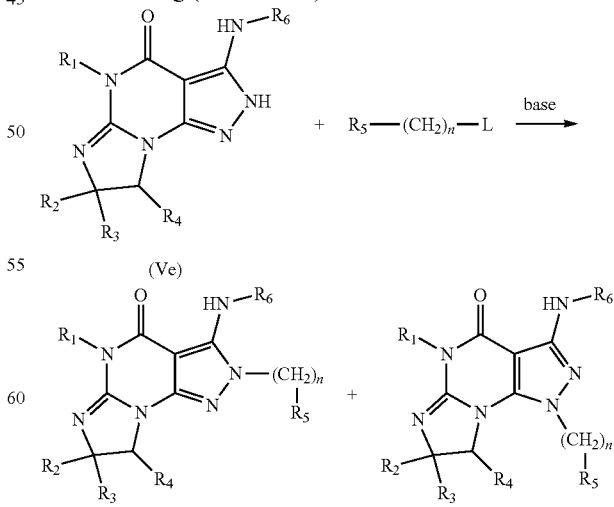

Compounds of Formula I wherein $R_1$, $R_2$, $R_3$, $R_4$, and $R_6$ are as defined previously for any of Formulae I, I(i), I(ii), or 1.1-1.73.

wherein R₅ is as defined previously for any of Formulae I, I(i), I(ii), or 1.1-1.73 and L is a leaving group such as a halogen, mesylate, or tosylate.

Methods of Using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1, thereby increasing intracellular levels of cAMP and cGMP, the Compounds of the Invention potentiate the activity of cyclic nucleotide synthesis inducers.

The invention provides methods of treatment of any one or more of the following conditions:

(i) Neurodegenerative diseases, including Parkinson's disease, restless leg, tremors, dyskinesias, Huntington's disease, Alzheimer's disease, and drug-induced movement disorders;

(ii) Mental disorders, including depression, attention deficit disorder, attention deficit hyperactivity disorder, bipolar illness, anxiety, sleep disorders, e.g., narcolepsy, cognitive impairment, e.g., cognitive impairment of schizophrenia, dementia, Tourette's syndrome, autism, fragile X syndrome, psychostimulant withdrawal, and drug addiction;

(iii) Circulatory and cardiovascular disorders, including cerebrovascular disease, stroke, congestive heart disease, hypertension, pulmonary hypertension, e.g., pulmonary arterial hypertension, and sexual dysfunction, including cardiovascular diseases and related disorders as described in International Application No. PCT/US2014/16741, the contents of which are incorporated herein by reference;

(iv) Respiratory and inflammatory disorders, including asthma, chronic obstructive pulmonary disease, and allergic rhinitis, as well as autoimmune and inflammatory diseases;

(v) Diseases that may be alleviated by the enhancement of progesterone-signaling such as female sexual dysfunction;

(vi) A disease or disorder such as psychosis, glaucoma, or elevated intraocular pressure;

(vii) Traumatic brain injury;

(viii) Any disease or condition characterized by low levels of cAMP and/or cGMP (or inhibition of cAMP and/or cGMP signaling pathways) in cells expressing PDE1; and/or (ix) Any disease or condition characterized by reduced dopamine D1 receptor signaling activity, comprising administering an effective amount of a Compound of the Invention, e.g., a compound according to any of Formulae I, I(i), I(ii), or 1.1-1.73, in free or pharmaceutically acceptable salt or prodrug form, to a human or animal patient in need thereof.

In an especially preferred embodiment, the invention provides methods of treatment or prophylaxis for narcolepsy. In this embodiment, PDE1 Inhibitors may be used as a sole therapeutic agent, but may also be used in combination or for co-administration with other active agents. Thus, the invention further comprises a method of treating narcolepsy comprising administering simultaneously, sequentially, or contemporaneously therapeutically effective amounts of (i) a PDE1 Inhibitor, e.g., a compound according to any of Formulae I, I(i), I(ii) or 1.1-1.73, and (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB), in free or pharmaceutically acceptable salt or prodrug form, to a human or animal patient in need thereof.

In another embodiment, the invention further provides methods of treatment or prophylaxis of a condition which may be alleviated by the enhancement of the progesterone signaling comprising administering an effective amount of a Compound of the Invention, e.g., a compound according to any of Formulae I, I(i), I(ii), or 1.1-1.73, in free or pharmaceutically acceptable salt or prodrug form, to a human or animal patient in need thereof. Diseases or conditions that may be ameliorated by enhancement of progesterone signaling include, but are not limited to, female sexual dysfunction, secondary amenorrhea (e.g., exercise amenorrhoea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmune disease, multiple sclerosis, prostate enlargement, prostate cancer, and hypothyroidism. For example, by enhancing progesterone signaling, the PDE1 inhibitors may be used to encourage egg implantation through effects on the lining of uterus, and to help maintain pregnancy in women who are prone to miscarriage due to immune response to pregnancy or low progesterone function. The novel PDE1 inhibitors, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this embodiment, PDE1 Inhibitors may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously therapeutically effective amounts of (i) a PDE1 Inhibitor, e.g., a compound according to any of Formulae I, I(i), I(ii), or 1.1-1.73, and (ii) a hormone, e.g., selected from estrogen and estrogen analogues (e.g., estradiol, estriol, estradiol esters) and progesterone and progesterone analogues (e.g., progestins)

in free or pharmaceutically acceptable salt or prodrug form, to a human or animal patient in need thereof.

The invention also provides a method for enhancing or potentiating dopamine D1 intracellular signaling activity in a cell or tissue comprising contacting said cell or tissue with an amount of a Compound of the Invention, e.g., a compound according to any of Formulae I, I(i), I(ii), or 1.1-1.73, in free or pharmaceutically acceptable salt or prodrug form, sufficient to inhibit PDE1 activity.

The invention also provides a method for treating a PDE1-related disorder, a dopamine D1 receptor intracellular signaling pathway disorder, or disorders that may be alleviated by the enhancement of the progesterone signaling pathway in a patient in need thereof comprising administering to the patient an effective amount of a Compound of the Invention, e.g., a compound according to any of Formulae I, I(i), I(ii), or 1.1-1.73, in free or pharmaceutically acceptable salt or prodrug form, that inhibits PDE1, wherein PDE1 activity modulates phosphorylation of DARPP-32 and/or the GluR1 AMPA receptor.

In another aspect, the invention also provides a method for the treatment for glaucoma or elevated intraocular pressure comprising topical administration of a therapeutically effective amount of a PDE1 Inhibitor of the Invention, e.g., a compound according to any of Formulae I, I(i), I(ii), or 1.1-1.73, in free or pharmaceutically acceptable salt form, in an ophthalmically compatible carrier to the eye of a patient in need thereof. However, treatment may alternatively include a systemic therapy. Systemic therapy includes treatment that can directly reach the bloodstream, or oral methods of administration, for example.

The invention further provides a pharmaceutical composition for topical ophthalmic use comprising a PDE1 inhibitor; for example an ophthalmic solution, suspension, cream or ointment comprising a PDE1 Inhibitor of the Invention, e.g., a compound according to any of Formulae I, I(i), I(ii) or 1.1-1.73, in free or ophthalmologically acceptable salt form, in combination or association with an ophthalmologically acceptable diluent or carrier.

Optionally, the PDE1 inhibitor may be administered sequentially or simultaneously with a second drug useful for treatment of glaucoma or elevated intraocular pressure. Where two active agents are administered, the therapeutically effective amount of each agent may be below the amount needed for activity as monotherapy. Accordingly, a sub-threshold amount (i.e., an amount below the level necessary for efficacy as monotherapy) may be considered therapeutically effective and may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

The invention thus provides the method of treatment of a condition selected from glaucoma and elevated intraocular pressure comprising administering to a patient in need thereof an effective amount, e.g., a subthreshold amount, of an agent known to lower intraocular pressure concomitantly, simultaneously or sequentially with an effective amount, e.g., a sub-threshold amount, of a PDE1 Inhibitor of the Invention, e.g., a compound according to any of Formulae I, I(i), I(ii) or 1.1-1.73, in free or pharmaceutically acceptable salt form, such that amount of the agent known to lower intraocular pressure and the amount of the PDE1 inhibitor in combination are effective to treat the condition.

In one embodiment, one or both of the agents are administered topically to the eye. Thus the invention provides a method of reducing the side effects of treatment of glaucoma or elevated intraocular pressure by administering a reduced dose of an agent known to lower intraocular pressure concomitantly, simultaneously or sequentially with an effective amount of a PDE1 inhibitor. However, methods other than topical administration, such as systemic therapeutic administration, may also be utilized.

The optional additional agent or agents for use in combination with a PDE1 inhibitor may, for example, be selected from the existing drugs comprise typically of instillation of a prostaglandin, pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine. Drugs currently used to treat glaucoma thus include, e.g., 1. Prostaglandin analogs such as latanoprost (Xalatan), bimatoprost (Lumigan) and travoprost (Travatan), which increase uveoscleral outflow of aqueous humor. Bimatoprost also increases trabecular outflow.
2. Topical beta-adrenergic receptor antagonists such as timolol, levobunolol (Betagan), and betaxolol, which decrease aqueous humor production by the ciliary body.
3. Alpha$_2$-adrenergic agonists such as brimonidine (Alphagan), which work by a dual mechanism, decreasing aqueous production and increasing uveo-scleral outflow.
4. Less-selective sympathomimetics like epinephrine and dipivefrin (Propine) increase outflow of aqueous humor through trabecular meshwork and possibly through uveoscleral outflow pathway, probably by a beta$_2$-agonist action.
5. Miotic agents (para-sympathomimetics) like pilocarpine work by contraction of the ciliary muscle, tightening the trabecular meshwork and allowing increased outflow of the aqueous humour.
6. Carbonic anhydrase inhibitors like dorzolamide (Trusopt), brinzolamide (Azopt), acetazolamide (Diamox) lower secretion of aqueous humor by inhibiting carbonic anhydrase in the ciliary body.
7. Physostigmine is also used to treat glaucoma and delayed gastric emptying.

For example, the invention provides pharmaceutical compositions comprising a PDE1 Inhibitor of the Invention, e.g., a compound according to any of Formulae I, I(i), I(ii), or 1.1-1.73, in free or pharmaceutically acceptable salt form, and an agent selected from (i) the prostanoids, unoprostone, latanoprost, travoprost, or bimatoprost; (ii) an alpha adrenergic agonist such as brimonidine, apraclonidine, or dipivefrin and (iii) a muscarinic agonist, such as pilocarpine, in combination or association with a pharmaceutically acceptable diluent or carrier. For example, the invention provides ophthalmic formulations comprising a PDE-1 Inhibitor of the Invention, e.g., a compound according to any of Formulae I, I(i), I(ii), or 1.1-1.73, together with bimatoprost, abrimonidine, brimonidine, timolol, or combinations thereof, in free or ophthamalogically acceptable salt form, in combination or association with an ophthamologically acceptable diluent or carrier. In addition to selecting a combination, however, a person of ordinary skill in the art can select an appropriate selective receptor subtype agonist or antagonist. For example, for alpha adrenergic agonist, one can select an agonist selective for an alpha 1 adrenergic receptor, or an agonist selective for an alpha$_2$ adrenergic receptor such as brimonidine, for example. For a beta-adrenergic receptor antagonist, one can select an antagonist selective for either $\beta_1$, or $\beta_2$, or $\beta_3$, depending on the appropriate therapeutic application. One can also select a muscarinic agonist selective for a particular receptor subtype such as $M_1$-$M_5$.

The PDE1 inhibitor may be administered in the form of an ophthalmic composition, which includes an ophthalmic solution, cream or ointment. The ophthalmic composition may additionally include an intraocular-pressure lowering agent.

In yet another example, the PDE1 Inhibitors disclosed may be combined with a subthreshold amount of an intraocular pressure-lowering agent which may be a bimatoprost ophthalmic solution, a brimonidine tartrate ophthalmic solution, or brimonidine tartrate/timolol maleate ophthalmic solution.

In addition to the above-mentioned methods, it has also been surprisingly discovered that PDE1 inhibitors are useful to treat psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder. Without intending to be bound by any theory, it is believed that typical and atypical antipsychotic drugs such as clozapine primarily have their antagonistic activity at the dopamine D2 receptor. PDE1 inhibitors, however, primarily act to enhance signaling at the dopamine D1 receptor. By enhancing D1 receptor signaling, PDE1 inhibitors can increase NMDA receptor function in various brain regions, for example in nucleus accumbens neurons and in the prefrontal cortex. This enhancement of function may be seen for example in NMDA receptors containing the NR2B subunit, and may occur e.g., via activation of the Src and protein kinase A family of kinases.

Therefore, the invention provides a new method for the treatment of psychosis, e.g., schizophrenia, schizoaffective disorder, schizophreniform disorder, psychotic disorder, delusional disorder, and mania, such as in acute manic episodes and bipolar disorder, comprising administering a therapeutically effective amount of a phosphodiesterase-1 (PDE1) Inhibitor of the Invention, e.g., a compound according to any of Formulae I, I(i), I(ii), or 1.1-1.73, in free or pharmaceutically acceptable salt form, to a patient in need thereof.

PDE 1 Inhibitors may be used in the foregoing methods of treatment prophylaxis as a sole therapeutic agent, but may also be used in combination or for co-administration with other active agents. Thus, the invention further comprises a method of treating psychosis, e.g., schizophrenia, schizoaffective disorder, schizophreniform disorder, psychotic disorder, delusional disorder, or mania, comprising administering simultaneously, sequentially, or contemporaneously therapeutically effective amounts of:
(i) a PDE1 Inhibitor of the invention, in free or pharmaceutically acceptable salt form; and
(ii) an antipsychotic, e.g.,
  Typical antipsychotics, e.g.,
    Butyrophenones, e.g. Haloperidol (Haldol, Serenace), Droperidol (Droleptan);
    Phenothiazines, e.g., Chlorpromazine (Thorazine, Largactil), Fluphenazine (Prolixin), Perphenazine (Trilafon), Prochlorperazine (Compazine), Thioridazine (Mellaril, Melleril), Trifluoperazine (Stelazine), Mesoridazine, Periciazine, Promazine, Triflupromazine (Vesprin), Levomepromazine (Nozinan), Promethazine (Phenergan), Pimozide (Orap);
    Thioxanthenes, e.g., Chlorprothixene, Flupenthixol (Depixol, Fluanxol), Thiothixene (Navane), Zuclopenthixol (Clopixol, Acuphase);
  Atypical antipsychotics, e.g.,
    Clozapine (Clozaril), Olanzapine (Zyprexa), Risperidone (Risperdal), Quetiapine (Seroquel), Ziprasidone (Geodon), Amisulpride (Solian), Paliperidone (Invega), Aripiprazole (Abilify), Bifeprunox; norclozapine,
in free or pharmaceutically acceptable salt form, to a patient in need thereof.

In a particular embodiment, the Compounds of the Invention are particularly useful for the treatment or prophylaxis of schizophrenia.

Compounds of the Invention, in free or pharmaceutically acceptable salt form, are particularly useful for the treatment of Parkinson's disease, schizophrenia, narcolepsy, glaucoma and female sexual dysfunction.

In still another aspect, the invention provides a method of lengthening or enhancing growth of the eyelashes by administering an effective amount of a prostaglandin analogue, e.g., bimatoprost, concomitantly, simultaneously or sequentially with an effective amount of a PDE1 inhibitor of the Invention, in free or pharmaceutically acceptable salt form, to the eye of a patient in need thereof.

In yet another aspect, the invention provides a method for the treatment or prophylaxis of traumatic brain injury comprising administering a therapeutically effective amount of a PDE1 Inhibitor of the Invention, e.g., a compound according to any of Formulae I, I(i), I(ii), or 1.1-1.73, in free or pharmaceutically acceptable salt form, to a patient in need thereof. Traumatic brain injury (TBI) encompasses primary injury as well as secondary injury, including both focal and diffuse brain injuries. Secondary injuries are multiple, parallel, interacting and interdependent cascades of biological reactions arising from discrete subcellular processes (e.g., toxicity due to reactive oxygen species, overstimulation of glutamate receptors, excessive influx of calcium and inflammatory upregulation) which are caused or exacerbated by the inflammatory response and progress after the initial (primary) injury.

The present invention also provides
(i) a Compound of the Invention, e.g., a compound according to any of Formulae I, I(i), I(ii), or 1.1-1.73, as hereinbefore described, in free or pharmaceutically acceptable salt form for example for use in any method or in the treatment of any disease or condition as hereinbefore set forth,
(ii) the use of a Compound of the Invention, e.g., a compound according to any of Formulae I, I(i), I(ii) or 1.1-1.73, as hereinbefore described, in free or pharmaceutically acceptable salt form, (in the manufacture of a medicament) for treating any disease or condition as hereinbefore set forth,
(iii) a pharmaceutical composition comprising a Compound of the Invention, e.g., a compound according to any of Formulae I, I(i), I(ii), or 1.1-1.73, as hereinbefore described, in free or pharmaceutically acceptable salt form, in combination or association with a pharmaceutically acceptable diluent or carrier, and
(iv) a pharmaceutical composition comprising a Compound of the Invention, e.g., a compound according to any of Formulae I, I(i), I(ii), or 1.1-1.73, as hereinbefore described, in free or pharmaceutically acceptable salt form, in combination or association with a pharmaceutically acceptable diluent or carrier for use in the treatment of any disease or condition as hereinbefore set forth.

Therefore, the invention provides use of a Compound of the Invention, e.g., a compound according to any of Formulae I, I(i), I(ii), or 1.1-1.73, as hereinbefore described, in free or pharmaceutically acceptable salt form, or a Compound of the Invention in a pharmaceutical composition form (in the manufacture of a medicament) for the treatment or prophylactic treatment of any one or more of the following diseases: Parkinson's disease, restless leg, tremors, dyskinesias, Huntington's disease, Alzheimer's disease, and/or drug-induced movement disorders; depression, attention deficit disorder, attention deficit hyperactivity disorder, bipolar illness, anxiety, sleep disorder, narcolepsy, cognitive impairment, e.g., cognitive impairment of schizophrenia, dementia, Tourette's syndrome, autism, fragile X syndrome, psychostimulant withdrawal, and/or drug addiction; cerebrovascular disease, stroke, congestive heart disease, hypertension, pulmonary hypertension, e.g., pulmonary arterial hypertension, and/or sexual dysfunction; asthma, chronic obstructive pulmonary disease, and/or allergic rhinitis, as well as autoimmune and inflammatory diseases; and/or female sexual dysfunction, exercise amenorrhoea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, hypothyroidism, and/or estrogen-induced endometrial hyperplasia and/or carcinoma; and/or any disease or condition characterized by low levels of cAMP and/or cGMP (or inhibition of cAMP and/or cGMP signaling pathways) in cells expressing PDE1, and/or by reduced dopamine D1 receptor signaling activity; and/or any disease or condition that may be ameliorated by the enhancement of progesterone signaling.

The invention also provides use of a Compound of the Invention, in free or pharmaceutically acceptable salt form, (the manufacture of a medicament) for the treatment or prophylactic treatment of any one or more of:
a) glaucoma, elevated intraocular pressure,
b) psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder,
c) traumatic brain injury, and/or
d) central and peripheral degenerative disorders particularly those with inflammatory components.

The phrase "Compounds of the Invention" or "PDE1 Inhibitor of the Invention" encompasses any and all of the compounds disclosed herewith, e.g., compounds according to any of Formulae I, I(i), I(ii) or 1.1-1.73, as hereinbefore described, in free or salt form.

The words "treatment" and "treating" are to be understood accordingly as embracing prophylaxis and treatment or amelioration of symptoms of disease as well as treatment of the cause of the disease. In one embodiment, the invention provides a method for the treatment of the disease or disorder disclosed herein. In another embodiment, the invention provides a method for the prophylaxis of a disease or disorder as disclosed herein.

For methods of treatment, the word "effective amount" is intended to encompass a therapeutically effective amount to treat a specific disease or disorder.

The term "pulmonary hypertension" is intended to encompass pulmonary arterial hypertension.

The term "patient" includes human or non-human (i.e., animal) patient. In one embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

Compounds of the Invention are in particular useful for the treatment of Parkinson's disease, narcolepsy and female sexual dysfunction.

Compounds of the Invention, in free or pharmaceutically acceptable salt form, may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease. In addition, the novel PDE1 inhibitors, e.g., as described herein, may also be administered in combination with estrogen/estradiol/estriol and/or progesterone/progestins to enhance the effectiveness of hormone replacement therapy or treatment of estrogen-induced endometrial hyperplasia or carcinoma.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

The synthetic methods for various Compounds of the Invention are illustrated below. The intermediates of Compounds of the Invention as well as other Compounds of the Invention (e.g., compounds of Formula 1.73) and their salts may be made using the methods as similarly described below and/or by methods similar to those generally described in the detailed description and by methods known in the chemical art.

Example 1

7,8-Dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one

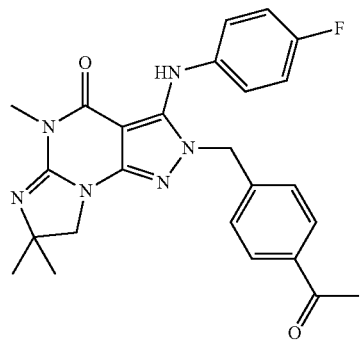 [SMILES: CC(=O)c1ccc(Cn2nc3c(c2Nc2ccc(F)cc2)C(=O)N(C)C2=NC(C)(C)CN23)cc1]

(a) 2-(4-Bromobenzyl)-7-(4-methoxybenzyl)-5-methyl-2H-pyrazolo[3,4-d]pyrimidine-4,6(5H,7H)-dione A suspension of 7-(4-methoxybenzyl)-5-methyl-2H-pyrazolo[3,4-d]pyrimidine-4,6(5H,7H)-dione (161 g, 562 mmol), 1-bromo-4-(bromomethyl)benzene (157 g, 628 mmol) and $K_2CO_3$ (93.2 g, 674 mmol) in DMF (800 mL) is stirred at room temperature until the reaction is complete. The reaction mixture is poured into water (5 L). After filtration, the filter cake is washed with water and ethanol successively, and then dried under vacuum to give 226 g of product (yield: 88%). MS (ESI) m/z 455.1 $[M+H]^+$.

(b) 2-(4-Bromobenzyl)-5-methyl-2H-pyrazolo[3,4-d]pyrimidine-4,6(5H,7H)-dione TFA (500 mL) is slowly added into a suspension of 2-(4-bromobenzyl)-7-(4-methoxybenzyl)-5-methyl-2H-pyrazolo[3,4-d]pyrimidine-4,6(5H,7H)-dione (226 g, 496 mmol) in methylene chloride (320 mL), and then TFMSA (160 mL) is added slowly. The reaction mixture is stirred at room temperature overnight. Solvents are removed under reduced pressure. The obtained residue is treated with water (4 L) and ethyl acetate (2 L), stirred at room temperature for 30 min, and then filtered. The filter cake is thoroughly washed with water to remove residual acids, followed by washing with ethyl acetate. The obtained white solids are dried in a heated oven to give 159 g of product (yield: 96%). MS (ESI) m/z 335.0 $[M+H]^+$.

(c) 6-Chloro-5-methyl-2-(4-bromobenzyl)-2H-pyrazolo[3,4-d]pyrimidin-4(5H)-one 2-(4-Bromobenzyl)-5-methyl-2H-pyrazolo[3,4-d]pyrimidine-4,6(5H,7H)-dione (159 g, 475 mmol) is suspended in $POCl_3$ (300 mL), and then slowly heated to reflux. After the mixture is refluxed for 60 h, $POCl_3$ is removed under reduced pressure. The obtained residue is dissolved in methylene chloride (5 L), cooled to 0° C., and then adjusted to pH 8-9 with saturated sodium bicarbonate. After filtration, the obtained solids are washed with water twice, and then dried under vacuum to give 157 g of product (yield: 94%). MS (ESI) m/z 353.0 $[M+H]^+$.

(d) 6-(1-Hydroxy-2-methylpropan-2-ylamino)-5-methyl-2-(4-bromobenzyl)-2H-pyrazolo[3,4-d]pyrimidin-4(5H)-one A mixture of 6-chloro-5-methyl-2-(4-bromobenzyl)-2H-pyrazolo[3,4-d]pyrimidin-4(5H)-one (157 g, 444 mmol) and 2-amino-2-methylpropan-1-ol (236 g, 2.65 mol) in NMP (1.3 L) is heated at 120-125° C. for 2 h, and then poured into cold water. After filtration, the filter cake is washed with water twice, and then dried under vacuum to give 134 g of product (yield: 74%). MS (ESI) m/z 406.1 $[M+H]^+$.

(e) 2-(4-Bromobenzyl)-7,8-dihydro-5,7,7-trimethyl-[2H]-imidazo-[1,2-a]pyrazolo[4,3-e]pyrimidin-4(5H)-one Thionyl chloride (67 mL, 922 mmol) is added dropwise to a solution of 6-(1-hydroxy-2-methylpropan-2-ylamino)-5-methyl-2-(4-bromobenzyl)-2H-pyrazolo[3,4-d]pyrimidin-4(5H)-one (134 g, 330 mmol) in DMF (800 mL). The reaction mixture is stirred at room temperature until the reaction is complete. The mixture is poured into cold water, and then adjusted to pH 8-9 with ammonium hydroxide aqueous solution. After filtration, the obtained solids are washed with water, and then dried under vacuum to give 118 g of product (yield: 92%). MS (ESI) 388.1 $[M+H]^+$.

(f) 2-(4-Phenoxybenzyl)-7,8-dihydro-5,7,7-trimethyl-[2H]-imidazo-[1,2-a]pyrazolo[4,3-e]pyrimidin-4(5H)-one 2-(4-Bromobenzyl)-7,8-dihydro-5,7,7-trimethyl-[2H]-imidazo-[1,2-a]pyrazolo[4,3-e]pyrimidin-4(5H)-one (118 g, 304 mmol) is added into a suspension of phenol (57 g, 606 mmol) and cesium carbonate (200 g, 614 mmol) in NMP (900 mL), followed by 2,2,6,6-tetramethylheptane-3,5-dione (7 mL, 33.5 mmol) and CuCl (15 g, 152 mmol). The reaction mixture is heated at 120° C. under argon atmosphere for 10 h. After the completion of the reaction, the mixture is diluted with water (4 L), and then extracted with ethyl acetate. The combined organic phase is evaporated to dryness. The obtained crude product is purified by silica gel column chromatography to give 103 g of product (yield: 84%). MS (ESI) m/z 402.2 $[M+H]^+$.

(g) 7,8-Dihydro-5,7,7-trimethyl-[2H]-imidazo-[1,2-a]pyrazolo[4,3-e]pyrimidin-4(5H)-one TFA (600 mL) is added into a suspension of 2-(4-phenoxybenzyl)-7,8-dihydro-5,7,7-trimethyl-[2H]-imidazo-[1,2-a]pyrazolo[4,3-e]pyrimidin-4(5H)-one (103 g, 257 mmol) in methylene chloride (210 mL) to give a tan solution, and then TFMSA (168 mL) is added. The reaction mixture is stirred at room temperature until the starting material disappears. The mixture is poured into cold water (3 L). After filtration, the filter cake is washed with water twice, and then basified with ammonium hydroxide aqueous solution, followed by adding ethyl acetate with stirring. The precipitated solids are filtered, washed successively with water three times, ethyl acetate twice and methanol once, and then dried under vacuum to give 45 g of product (yield: 80%). MS (ESI) m/z 220.2 $[M+H]^+$.

(h) 7,8-Dihydro-2-(4-acetylbenzyl)-5,7,7-trimethyl-[2H]-imidazo-[1,2-a]pyrazolo[4,3-e]pyrimidin-4(5H)-one A suspension of 7,8-dihydro-5,7,7-trimethyl-[2H]-imidazo-[1,2-a]pyrazolo[4,3-e]pyrimidin-4(5H)-one (438 mg, 2.0 mmol), 1-(4-(bromomethyl)phenyl)ethanone (520 mg, 2.4 mmol) and $K_2CO_3$ (828 mg, 6.0 mmol) in DMF (18 mL) is stirred at room temperature over a weekend. Solvent is removed under reduced pressure. The obtained residue is purified on a basic alumina oxide column to give 634 mg of product (yield: 90%). MS (ESI) m/z 352.2 $[M+H]^+$.

(i) 7,8-Dihydro-2-(4-acetylbenzyl)-3-chloro-5,7,7-trimethyl-[2H]-imidazo-[1,2-a]pyrazolo[4,3-e]pyrimidin-4(5H)-one 1.0M LiHMDS (2.5 mL, 2.5 mmol) in THF is added dropwise into a solution of 7,8-dihydro-2-(4-acetylbenzyl)-5,7,7-trimethyl-[2H]-imidazo-[1,2-a]pyrazolo[4,3-e]pyrimidin-4(5H)-one (580 mg, 1.65 mmol) and hexachloroethane (782 mg, 3.32 mmol) in methylene chloride (8 mL) at −20° C. The reaction mixture is stirred at −20° C. for 30 min, and then quenched with acetic acid (60 μL). Solvents are removed under reduced pressure and the obtained residue is purified on a basic alumina oxide column to give 273 mg of product (yield: 43%). MS (ESI) m/z 386.2 [M+H]⁺.

(j) 7,8-Dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one 7,8-Dihydro-2-(4-acetylbenzyl)-3-chloro-5,7,7-trimethyl-[2H]-imidazo-[1,2-a]pyrazolo[4,3-e]pyrimidin-4(5H)-one (150 mg, 0.389 mmol), 4-fluorobenzenamine (41 μL, 0.428 mmol) and potassium carbonate (107 mg, 0.775 mmol) in tert-amyl alcohol (1.3 mL) are degassed with argon and then Xantphos (9.0 mg, 0.016 mmol) and Pd₂(dba)₃ (7.13 mg, 0.0078 mmol) are added. The suspension is degassed again, and then heated to 110° C. The reaction mixture is stirred at 110° C. under argon for 24 h. After routine workup, the crude mixture is purified with a semi-preparative HPLC to give 107 mg of the final product as a formate salt (HPLC purity: 96%; yield: 54%). ¹H NMR (500 MHz, Chloroform-d) δ 8.20 (s, 1H), 7.84 (d, J=8.3 Hz, 2H), 7.06-7.00 (m, 3H), 6.99-6.92 (m, 2H), 6.92-6.86 (m, 2H), 4.91 (s, 2H), 3.77 (s, 2H), 3.37 (s, 3H), 2.57 (s, 3H), 1.48 (s, 6H). MS (ESI) m/z 461.2 [M+H]⁺.

Example 2

7,8-Dihydro-2-(4-(1-hydroxyethyl)benzyl)-3-(4-fluorophenylamino)-5,7,7-trimethyl-[2H]-imidazo-[1,2-a]pyrazolo[4,3-e]pyrimidin-4(5H)-one

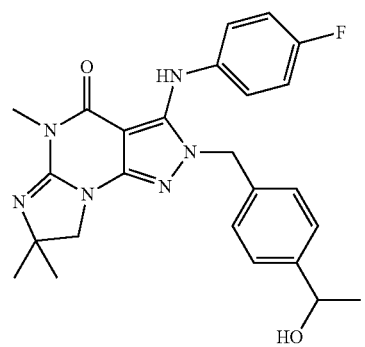 [SMILES: CC(O)c1ccc(Cn2nc3c(c2Nc2ccc(F)cc2)C(=O)N(C)C2=NC(C)(C)CN23)cc1]

NaBH₄ (18 mg, 0.48 mmol) is slowly added to a solution of 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one (22 mg, 0.048 mmol) in methanol (1 mL) at −20° C. The reaction mixture is stirred at −10° C. for 3 h, and then quenched with water (0.5 mL). After filtration, the obtained crude product is purified by a semi-preparative HPLC to give 20 mg of pure product as a formate salt (HPLC purity: 98%; yield: 82%). ¹H NMR (400 MHz, DMSO-d6) δ 8.64 (s, 1H), 8.15 (s, 1H), 7.24 (d, J=8.1 Hz, 2H), 7.05 (d, J=8.2 Hz, 2H), 7.03-6.94 (m, 2H), 6.82-6.73 (m, 2H), 5.13 (s, 2H), 4.66 (q, J=6.5 Hz, 1H), 3.58 (s, 2H), 3.17 (s, 1H), 3.08 (s, 3H), 1.34-1.19 (m, 9H). MS (ESI) m/z 463.2 [M+H]⁺

Example 3

7,8-Dihydro-2-(4-acetylbenzyl)-3-(3,4-difluorophenylamino)-5,7,7-trimethyl-[2H]-imidazo-[1,2-a]pyrazolo[4,3-e]pyrimidin-4(5H)-one

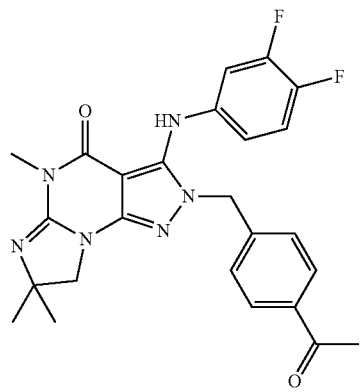 [SMILES: CC(=O)c1ccc(Cn2nc3c(c2Nc2ccc(F)c(F)c2)C(=O)N(C)C2=NC(C)(C)CN23)cc1]

The synthesis method is analogous to example 1 wherein 3,4-difluorobenzenamine is added in step (j) instead of 4-fluorobenzenamine. Final product is obtained as a formate salt (HPLC purity: 99%). ¹H NMR (500 MHz, DMSO-d6) δ 8.86 (s, 1H), 8.15 (s, 1H), 7.88 (d, J=8.3 Hz, 2H), 7.32-7.12 (m, 3H), 6.72 (ddd, J=12.8, 6.9, 2.7 Hz, 1H), 6.57 (m, 1H), 5.28 (s, 2H), 3.58 (s, 2H), 3.10 (s, 3H), 2.53 (s, 3H), 1.26 (s, 6H). MS (ESI) m/z 479.2 [M+H]⁺

Example 4

7,8-Dihydro-2-(4-acetylbenzyl)-3-(4-fluoro-3-methylphenylamino)-5,7,7-trimethyl-[2H]-imidazo-[1,2-a]pyrazolo[4,3-e]pyrimidin-4(5H)-one

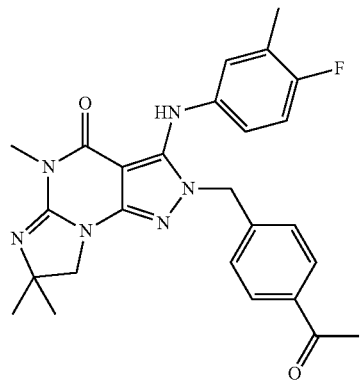 [SMILES: CC(=O)c1ccc(Cn2nc3c(c2Nc2ccc(F)c(C)c2)C(=O)N(C)C2=NC(C)(C)CN23)cc1]

The synthesis method is analogous to example 1 wherein 4-fluoro-3-methylbenzenamine is added in step (j) instead of 4-fluorobenzenamine. Final product is obtained as a formate salt (HPLC purity: 98%). ¹H NMR (500 MHz, Chloroform-d) δ 8.15 (s, 1H), 7.84 (d, J=8.3 Hz, 2H), 7.04 (d, J=8.3 Hz, 2H), 6.96-6.85 (m, 2H), 6.79-6.66 (m, 2H), 4.89 (s, 2H), 3.75 (s, 2H), 3.40 (s, 3H), 2.57 (s, 3H), 2.11 (d, J=1.8 Hz, 3H), 1.47 (s, 6H). MS (ESI) m/z 475.2 [M+H]+

Example 5

Measurement of PDE1 Inhibition In Vitro Using IMAP Phosphodiesterase Assay Kit

Phosphodiesterase 1 (PDE1) is a calcium/calmodulin dependent phosphodiesterase enzyme that converts cyclic guanosine monophosphate (cGMP) to 5'-guanosine monophosphate (5'-GMP). PDE1 can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization ($\Delta$mp). Inhibition of phosphodiesterase, therefore, is detected as a decrease in $\Delta$mp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: The following phosphodiesterase enzymes may be used: 3',5'-cyclic-nucleotide-specific bovine brain phosphodiesterase (Sigma, St. Louis, Mo.) and recombinant full length human PDE1A and PDE1B (r-hPDE1A and r-hPDE1B, respectively) which may be produced e.g., in HEK or SF9 cells by one skilled in the art. The PDE1 enzyme is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. The test compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization ($\Delta$mp).

A decrease in GMP concentration, measured as decreased $\Delta$mp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus $\Delta$mP, which allows $IC_{50}$ values to be estimated using nonlinear regression software (XLFit; IDBS, Cambridge, Mass.).

The Compounds of the Invention may be selected and tested in an assay as described or similarly described herein for PDE1 inhibitory activity. Exemplified Compounds of the Invention (e.g., compounds of Examples 1, 2, 3, and 4) have $IC_{50}$ values of less than or equal to 5 nm. $K_i$ values for Exemplified Compounds of the Invention are as shown in Table 1 below.

TABLE 1

| Example | r-hPDE1A - $K_i$ (μm) | r-hPDE1B - $K_i$ (μm) |
| --- | --- | --- |
| 1 | 0.0002 | 0.001 |
| 2 | 0.0005 | 0.004 |
| 3 | 0.0003 | 0.004 |
| 4 | 0.0001 | 0.0004 |

Example 6

Novel Object Recognition Assay

To measure the cognition-enhancing effects of the compounds of the invention, the candidate compounds may be evaluated in a Novel Object Recognition (NOR) assay. This assay protocol is described in detail in Ennaceur et al., *Behav. Brain Res.* (1988) 31:47-59 and Prickaerts et al., *Eur. J. Pharmacol.* (1997) 337:125-136, the contents of each of which are incorporated by reference in their entirety. In this protocol, the rats are introduced to a chamber at time T1 and allowed to interrogate two identical "familiar objects" for six minutes. Twenty-four hours later, they are re-introduced to this chamber, where one of the familiar objects has been replaced with a novel object. The "discrimination index", a measure of the time spent in close proximity to the novel over the familiar object, may then be measured. Since rodents will forget the original experiment at T1 within 4 hours, this test with a 24 h interval is a measure of strong cognitive enhancement.

This assay protocol can be modified in order to evaluate different phases of memory. There are three general phases of memory, namely, acquisition, consolidation and retrieval. In this modified protocol, the rats may be dosed with the candidate compound two hours before T1 and tested 24 h later without additional dosing. This is a test of the acquisition process. In addition, administration at various other times after the T1 test may be done to understand the compound's effectiveness in memory consolidation and recall. Specifically, these dosing times represent acquisition (T1−2 h), early consolidation (T1+0.1 h), late consolidation (T1+3 h), and retrieval (T2−2 h).

Using the protocol described above or similarly described above, the compound of Example 1 is shown to have a minimal effective dose of 0.1 mg/kg PO when administering to a rat 2 hours before T1.

Example 7

PDE1 Inhibitor Effect on Sexual Response in Female Rats

The effect of PDE1 inhibitors on Lordosis Response in female rats may be measured as described in Mani, et al.,

*Science* (2000) 287: 1053, the contents of which are incorporated herein by reference. Ovariectomized and cannulated wild-type rats are primed with 2 μg estrogen followed 24 hours later by intracerebroventricular (icv) injection of progesterone (2 μg), PDE1 Inhibitors of the Invention (0.1 mg, 1.0 mg or 2.5 mg) or sesame oil vehicle (control). The rats may be tested for lordosis response in the presence of male rats. Lordosis response is quantified by the lordosis quotient (LQ=number of lordosis/10 mounts×100).

Example 8

Haloperidol Induced Catalepsy Model

To evaluate the potential beneficial effects to motor defects present in schizophrenics treated with typical and atypical antipsychotic agents and in Parkinson's disease patients, the compounds of the invention may be tested in a reversal of catalepsy model in which motor freezing, or catalepsy, is induced by potent dopamine D2 receptor antagonists such as haloperidol or risperidone. The method uses the "bar grip test", in which the front paws of the mouse are placed so as to grip a 3 mm-diameter, suspended wooden bar. A "step down latency" is measured by recording the time until the mouse removes its paws from the wooden bar to the floor surface. Catalepsy is a freezing of the musculature that prevents the mouse from moving off the bar. Reduction in the catalepsy induced in this model will indicate that the compound will have a beneficial effect both in schizophrenia where extrapyramidal side effects are frequent and in Parkinson's disease.

A total of seventeen (17) eight week-old, male C57BL/6 mice (Jackson Laboratories) are used in a typical experiment testing the effect of the compound of Example 1. Mice are divided into six (6) groups (N=2 for vehicle group; N=3 mice/drug-treated group), receiving the following treatments: Vehicle alone, haloperidol alone (3 mg/Kg PO), Compound of Example 1 alone (0.3 mg/Kg PO), haloperidol (3 mg/Kg PO)+Compound of Example 1 (0.1 mg/Kg PO), haloperidol (3 mg/Kg PO)+Compound of Example 1 (0.3 mg/Kg PO), or haloperidol (3 mg/Kg PO)+Compound of Example 1 (1 mg/Kg PO). A catalepsy score is recorded for each mouse at 2, 3, 4, and 6 hours after administration of drugs. The chamber used for measuring catalepsy is comprised of a Plexiglas cage outfitted with a 3 mm-diameter wooden bar fixed horizontally 4 cm above the floor of cage. For each test session, both forepaws of the mouse are placed on the bar while the hind paws are on the Plexiglas floor. The latency until the mouse steps both paws down from the bar to the floor surface (i.e., step down latency) is recorded up to 120 sec. If the mouse steps off immediately (less than 10 sec after placement), another attempt is made up to a maximum of 10 attempts. If none of the 10 attempts are beyond 10 sec, the longest duration recorded is used as the catalepsy score. Otherwise, the initial cataleptic duration (>10 sec) is recorded during the 120 sec testing time. Mean step down latency is calculated for each treatment group. The effect of the compound of Example 1 on step down latency after haloperidol treatment is statistically evaluated by comparing group differences by analysis of variance (ANOVA, $F_{5,16}$) followed by application of Newman-Keuls post-hoc multiple comparison tests at each time point across all doses tested.

By using the protocol described or similarly described in this example, the compound of Example 1 is shown to be active in a catalepsy model with a minimal effective dose of 0.1 mg/Kg.

Example 9

Measurement of Metabolism Rates in Human Liver Microsomes Stability Protocol

Pooled human liver microsomes (final protein concentration 0.5 mg/ml) are incubated with test compound (final concentration 1 μM) in the presence of a NADPH regenerating system. The final buffer composition is: 1 mM EDTA, 100 mM potassium phosphate pH 7.5. The reactions are initiated by addition of the cofactor NADPH, and terminated after a 0, 15, 30, 45 and 60 minute incubation at 37° C. by addition of cold acetonitrile containing the internal analysis standard. After centrifuging at 4000 rpm for 20 minutes at 4° C., the supernatant are transferred for analysis using HPLC/MS/MS to measure the disappearance of the test compound. The percentage of the test compound remaining over time is calculated relative to the zero time point. The intrinsic clearance rates were calculated based on percentage of compound remaining at the 15-60 min. time points.

By using the protocol described or similarly described in this example, the compound of Example 1 is shown to have a $T_{1/2}$ of 171 minutes, the compound of Example 3 is shown to have a $T_{1/2}$ of 78 minutes, and the compound of Example 4 is shown to have a $T_{1/2}$ of 67 minutes.

What is claimed is:

1. A compound of Formula I:

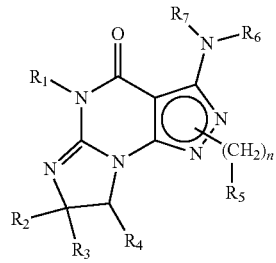

Formula I wherein
(i) $R_1$ is H or $C_{1-4}$ alkyl;
(ii) $R_2$ and $R_3$ are independently H or $C_{1-6}$ alkyl;
(iii) $R_4$ is H or $C_{1-4}$ alkyl;
(iv) $R_5$ is aryl optionally substituted with one or more groups independently selected from —C(=O)—$C_{1-6}$ alkyl and $C_{1-6}$-hydroxyalkyl;
(v) $R_6$ and $R_7$ are independently H or aryl optionally substituted with one or more groups independently selected from $C_{1-6}$ alkyl and halogen; and
(vi) n is 1, 2, 3, or 4,
in free or salt form.

2. The compound according to claim 1, wherein the compound is a compound of Formula I(i):

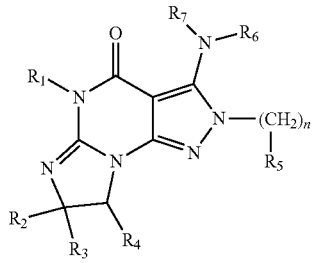

Formula I(i)

wherein
(i) $R_1$ is H or $C_{1-4}$ alkyl;
(ii) $R_2$ and $R_3$ are independently H or $C_{1-6}$ alkyl;
(iii) $R_4$ is H or $C_{1-4}$ alkyl;
(iv) $R_5$ is aryl optionally substituted with one or more groups independently selected from —C(=O)—$C_{1-6}$ alkyl and $C_{1-6}$-hydroxyalkyl;
(v) $R_6$ and $R_7$ are independently H or aryl optionally substituted with one or more groups independently selected from $C_{1-6}$ alkyl and halogen; and
(vi) n is 1, 2, 3, or 4,
in free or salt form.

3. The compound according to claim 1, wherein the compound is a compound of Formula I(ii):

Formula I(ii)

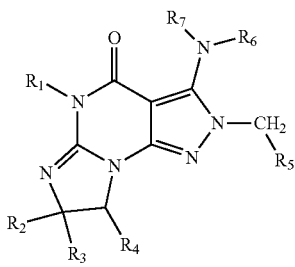

wherein
(i) $R_1$ is H or $C_{1-4}$ alkyl;
(ii) $R_2$ and $R_3$ are independently H or $C_{1-6}$ alkyl;
(iii) $R_4$ is H or $C_{1-4}$ alkyl;
(iv) $R_5$ is aryl optionally substituted with one or more groups independently selected from —C(=O)—$C_{1-6}$ alkyl and $C_{1-6}$-hydroxyalkyl; and
(v) $R_6$ and $R_7$ are independently H or aryl optionally substituted with one or more groups independently selected from $C_{1-6}$ alkyl and halogen,
in free or salt form.

4. The compound according to claim 3, wherein
(i) $R_1$ is $C_{1-4}$ alkyl;
(ii) $R_2$ and $R_3$ are independently $C_{1-6}$ alkyl;
(iii) $R_4$ is H;
(iv) $R_5$ is aryl substituted with one or more groups independently selected from —C(=O)—$C_{1-6}$ alkyl and $C_{1-6}$-hydroxyalkyl;
(v) $R_6$ is aryl substituted with one or more groups independently selected from $C_{1-6}$ alkyl and halogen; and
(vi) $R_7$ is H,
in free or salt form.

5. The compound according to claim 1, wherein the compound is selected from

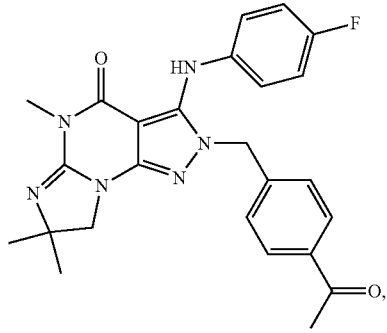

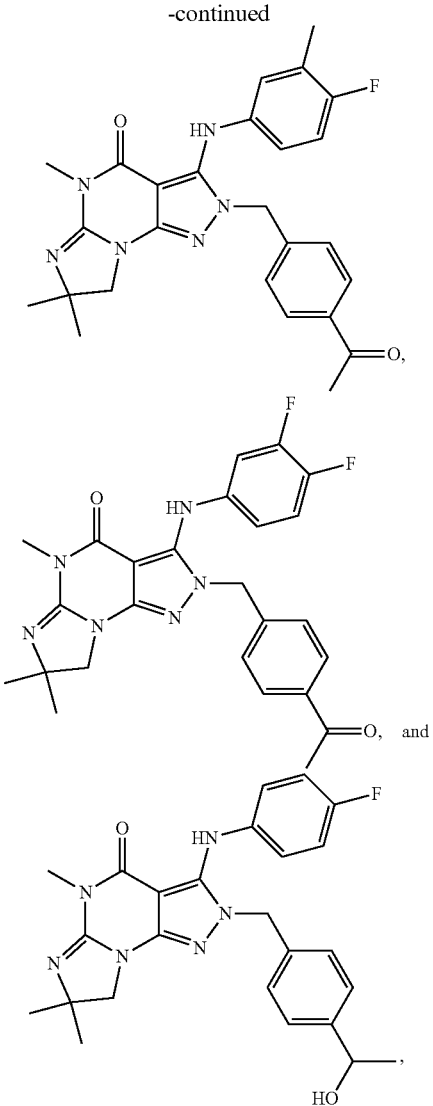

in free or salt form.

6. A pharmaceutical composition comprising a compound according to claim 1, in free or pharmaceutically acceptable salt form, in admixture with a pharmaceutically acceptable diluent or carrier.

7. The compound according to claim 1, wherein the compound is

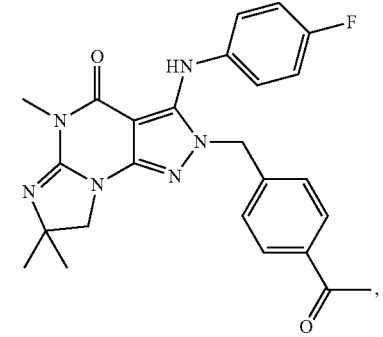 [SMILES: CC(=O)c1ccc(Cn2nc3c(c2Nc2ccc(F)cc2)C(=O)N(C)C2=NC(C)(C)CN23)cc1]

in free or salt form.

8. The compound according to claim 1, wherein the compound is

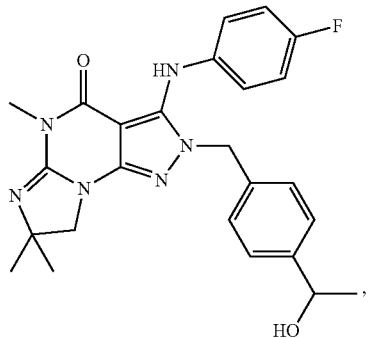 [SMILES: CC(O)c1ccc(Cn2nc3c(c2Nc2ccc(F)cc2)C(=O)N(C)C2=NC(C)(C)CN23)cc1]

in free or salt form.

9. The compound according to claim 1, wherein the compound is

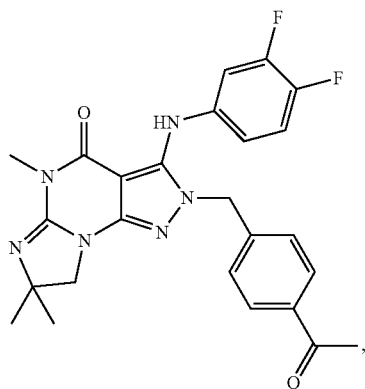 [SMILES: CC(=O)c1ccc(Cn2nc3c(c2Nc2ccc(F)c(F)c2)C(=O)N(C)C2=NC(C)(C)CN23)cc1]

in free or salt form.

10. The compound according to claim 1, wherein the compound is

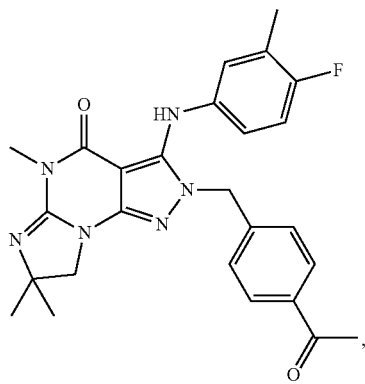 [SMILES: CC(=O)c1ccc(Cn2nc3c(c2Nc2ccc(F)c(C)c2)C(=O)N(C)C2=NC(C)(C)CN23)cc1]

in free or salt form.

11. The compound according to claim 3, wherein
 (i) $R_5$ is phenyl optionally substituted with one or more groups independently selected from —C(=O)—$C_{1-6}$ alkyl and $C_{1-6}$-hydroxyalkyl; and
 (ii) $R_6$ and $R_7$ are independently H or phenyl optionally substituted with one or more groups independently selected from $C_{1-6}$ alkyl and halogen,
in free or salt form.

12. The compound according to claim 11, wherein
 (i) $R_1$ is $C_{1-4}$ alkyl;
 (ii) $R_2$ and $R_3$ are independently $C_{1-6}$ alkyl;
 (iii) $R_4$ is H;
 (iv) $R_5$ is phenyl substituted with one or more groups independently selected from —C(=O)—$C_{1-6}$ alkyl and $C_{1-6}$-hydroxyalkyl;
 (v) $R_6$ is phenyl substituted with one or more groups independently selected from $C_{1-6}$ alkyl and halogen; and
 (vi) $R_7$ is H,
in free or salt form.

13. The compound according to claim 7, wherein the compound is a pharmaceutically acceptable salt.

14. The compound according to claim 8, wherein the compound is a pharmaceutically acceptable salt.

15. The compound according to claim 9, wherein the compound is a pharmaceutically acceptable salt.

16. The compound according to claim 10, wherein the compound is a pharmaceutically acceptable salt.

17. A pharmaceutical composition comprising a compound according to claim 4, in free or pharmaceutically acceptable salt form, in admixture with a pharmaceutically acceptable diluent or carrier.

18. A pharmaceutical composition comprising a compound according to claim 12, in free or pharmaceutically acceptable salt form, in admixture with a pharmaceutically acceptable diluent or carrier.

19. A pharmaceutical composition comprising the compound according to claim 7, in free or pharmaceutically acceptable salt form, in admixture with a pharmaceutically acceptable diluent or carrier.

20. A pharmaceutical composition comprising the compound according to claim 8, in free or pharmaceutically acceptable salt form, in admixture with a pharmaceutically acceptable diluent or carrier.

21. A pharmaceutical composition comprising the compound according to claim 9, in free or pharmaceutically acceptable salt form, in admixture with a pharmaceutically acceptable diluent or carrier.

22. A pharmaceutical composition comprising the compound according to claim 10, in free or pharmaceutically acceptable salt form, in admixture with a pharmaceutically acceptable diluent or carrier.

* * * * *